US009237912B2

(12) United States Patent
Dell'Oca

(10) Patent No.: US 9,237,912 B2
(45) Date of Patent: Jan. 19, 2016

(54) MINIMALLY INVASIVE IMPLANT AND CRIMPING SYSTEM

(71) Applicant: DePuy Synthes Products, LLC, Raynham, MA (US)

(72) Inventor: Alberto A. Fernandez Dell'Oca, Montevideo (UY)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 310 days.

(21) Appl. No.: 13/914,789

(22) Filed: Jun. 11, 2013

(65) Prior Publication Data

US 2013/0274812 A1    Oct. 17, 2013

Related U.S. Application Data

(63) Continuation of application No. 12/999,765, filed as application No. PCT/US2009/051356 on Jul. 22, 2009, now Pat. No. 8,496,659.

(60) Provisional application No. 61/083,546, filed on Jul. 25, 2008, provisional application No. 61/084,298, filed on Jul. 29, 2008, provisional application No. 61/085,437, filed on Aug. 1, 2008.

(51) Int. Cl.
| A61B 17/56 | (2006.01) |
| A61B 17/58 | (2006.01) |
| A61B 17/82 | (2006.01) |
| A61F 2/30 | (2006.01) |
| A61B 17/84 | (2006.01) |
| A61B 17/88 | (2006.01) |

(52) U.S. Cl.
CPC ............... *A61B 17/82* (2013.01); *A61B 17/842* (2013.01); *A61B 17/8863* (2013.01); *A61B 17/8869* (2013.01)

(58) Field of Classification Search
USPC ......... 606/280, 70, 282, 74, 286, 324; 72/402
See application file for complete search history.

(56) References Cited

U.S. PATENT DOCUMENTS 3,399,605 A * 9/1968 Landers ................. E21B 17/05
                                                    192/69.71
4,262,391 A    4/1981 Peash
(Continued)

FOREIGN PATENT DOCUMENTS

WO    2007047467 A1    4/2007

*Primary Examiner* — David Bates
*Assistant Examiner* — Olivia C Chang
(74) *Attorney, Agent, or Firm* — Fay Kaplun & Marcin, LLP

(57) ABSTRACT

A device for treating a bone comprises a cable block including a first lumen extending from a first proximal opening in a proximal face of the cable block to a first distal opening in a distal face thereof, the first lumen being configured to receive a cerclage cable including an enlarged end. The cable block further includes a second lumen extending from a second proximal opening in the proximal face to a second distal opening in the distal face and being configured to receive a portion of the cable extending from the enlarged end while preventing the enlarged end from passing therethrough. The cable block includes a slot connecting distal portions of the first and second lumens and being at least as large as the second lumen in combination with a crimpable locking member including a channel configured to receive the portion of the cable extending from the enlarged end.

11 Claims, 24 Drawing Sheets

(56) References Cited

U.S. PATENT DOCUMENTS

| | | |
|---|---|---|
| 5,190,545 A | 3/1993 | Corsi et al. |
| 5,569,253 A * | 10/1996 | Farris et al. .................... 606/74 |
| 5,702,399 A | 12/1997 | Kilpela et al. |
| 2004/0087954 A1 * | 5/2004 | Allen et al. .................... 606/74 |

* cited by examiner

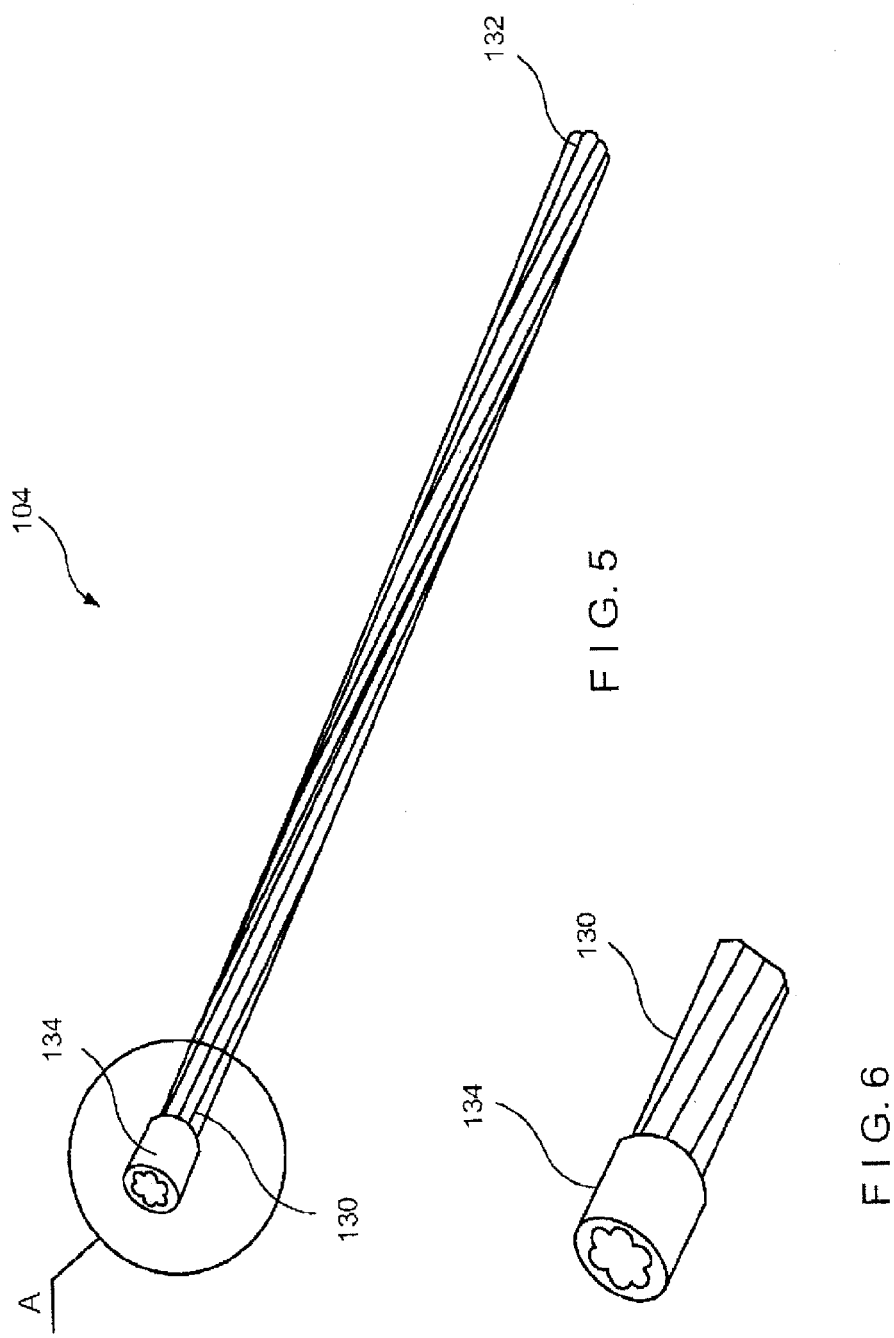

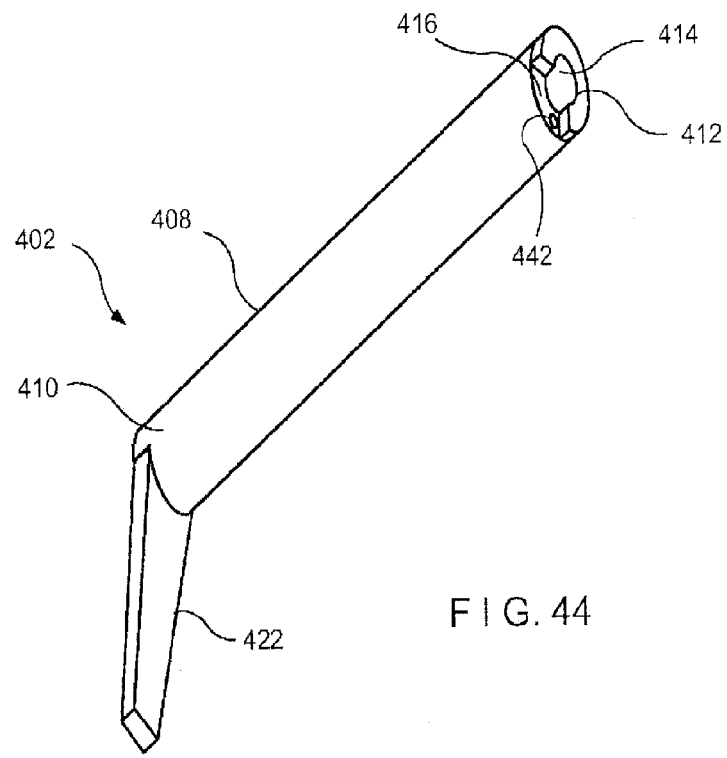
FIG. 44
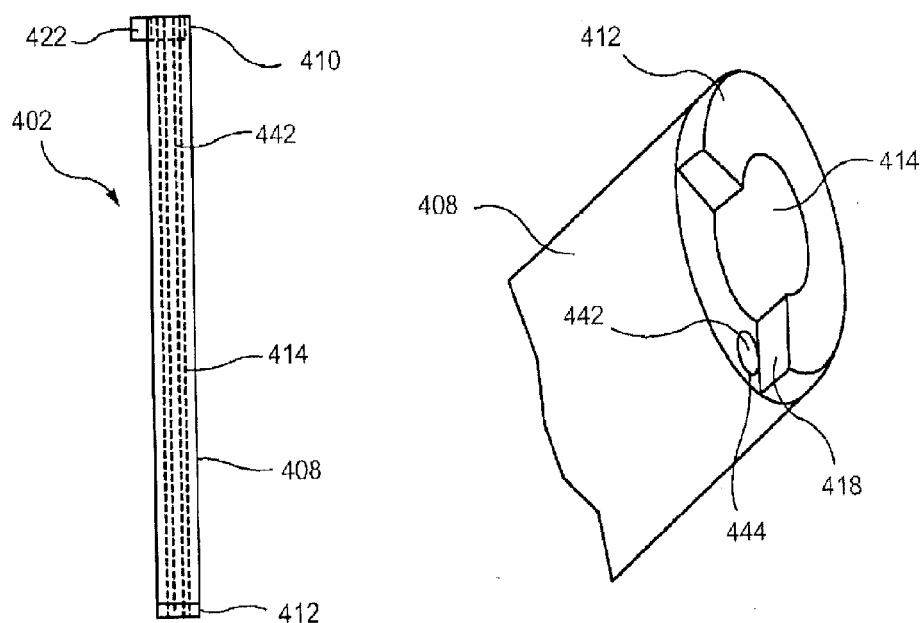
FIG. 45
FIG. 46

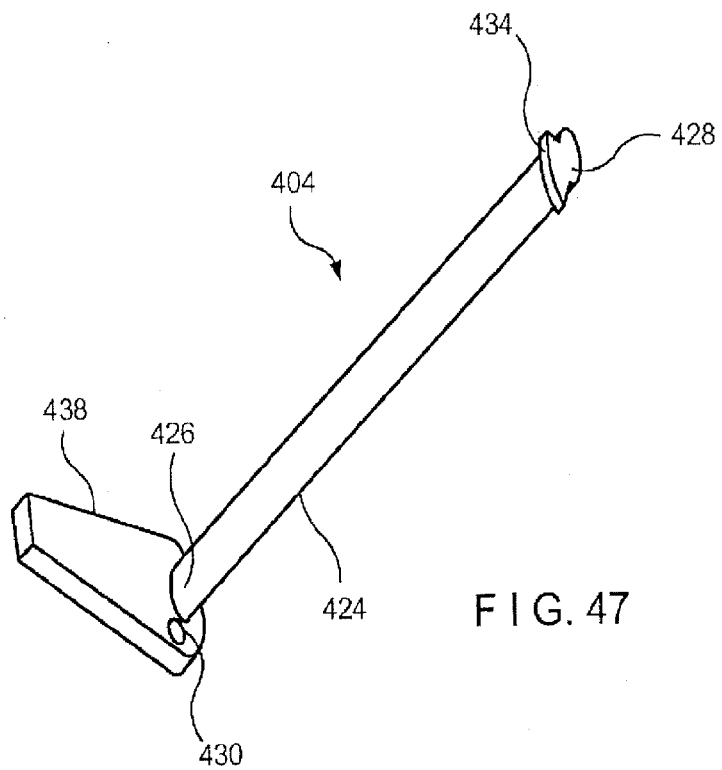
FIG. 47
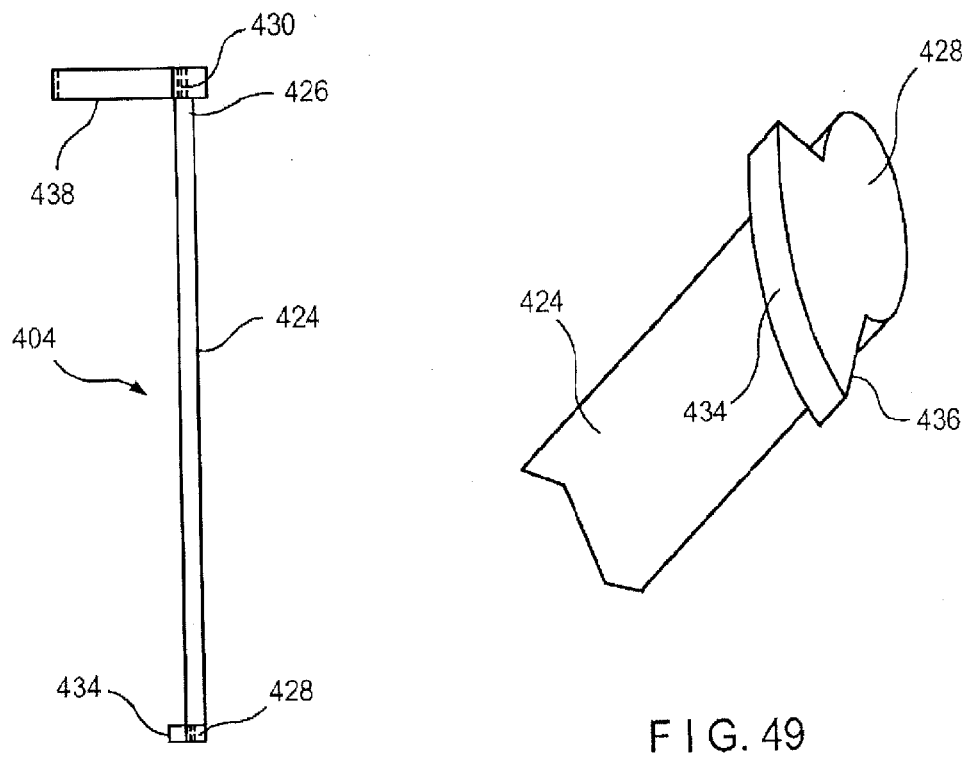
FIG. 48
FIG. 49

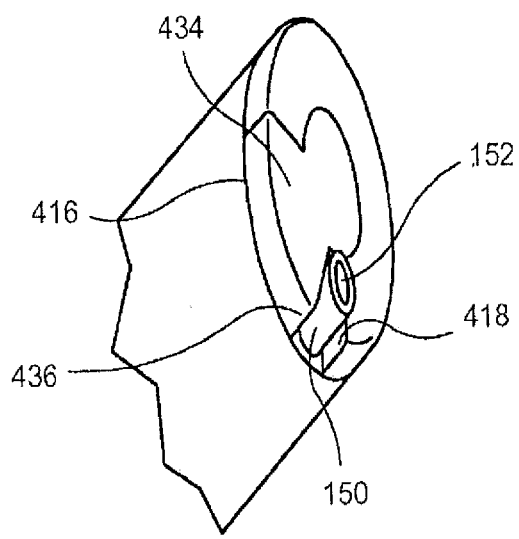
F I G. 50
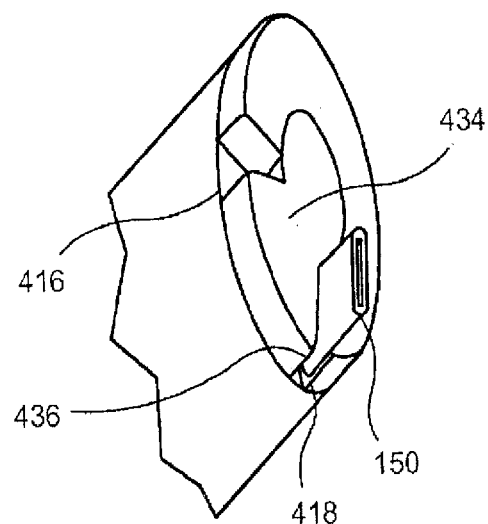
F I G. 51

MINIMALLY INVASIVE IMPLANT AND CRIMPING SYSTEM

PRIORITY CLAIM

This application claims priority to U.S. Provisional Application Ser. No. 61/083,546 entitled "Minimally Invasive Implant for Periprosthetic Fractures" filed on Jul. 25, 2008, U.S. Provisional Application Ser. No. 61/084,298 entitled "Minimally Invasive Crimp and Cable, Its Crimping-Cutting Tool and the System to Do it" filed Jul. 29, 2008 and U.S. Provisional Application Ser. No. 61/085,437 entitled "Minimally Invasive Crimp and Cable, Its Crimping Tool and the System to Do it" filed on Aug. 1, 2008. The entire specifications of the above-identified applications are expressly incorporated herein by reference.

FIELD OF THE INVENTION

The present invention relates to the treatment of a bone and, in particular, to a minimally invasive treatment of a fracture by circling a cable around the fractured bone and crimping a crimp over the cable to hold the cable in place via a small incision through the skin.

BACKGROUND

Peri-prosthetic fractures of the femur are common injuries that may be very difficult to treat. For example, a previously placed implant may interfere with the healing or placement of other bone fixation elements. One system of treating a peri-prosthetic fracture loops a cable around the bone to secure a fractured portion of the bone. These cables are often used in conjunction with implants that may be positioned along the bone to provide stability to the bone. However, the cables often slide along the implant which may result in difficult positioning the cable about a desired area of the bone. In addition, securing the cable after it has been looped around the bone often requires a large surgical approach, which may result in greater risks to the patient.

SUMMARY OF THE INVENTION

The present invention is directed to a device for treating a bone comprising a cable block including a first lumen extending from a first lumen proximal opening in a proximal face of the cable block to a first lumen distal opening in a distal face of the cable block, the first lumen being sized and shaped to slidably receive therethrough a cerclage cable including an enlarged end, the cable block further including a second lumen extending from a second lumen proximal opening in the proximal face of the cable block to a second lumen distal opening in the distal face of the cable block, the second lumen being sized and shaped to receive therethrough a portion of the cable extending from the enlarged end while preventing the enlarged end from passing therethrough, the cable block including a slot connecting distal portions of the first and second lumens, the slot being at least as large in diameter as the second lumen in combination with a locking member including a channel sized to slidably receive the portion of the cable extending from the enlarged end and a proximal abutting surface configured to abut a portion of a proximal face of the cable block surrounding the second lumen proximal opening, the locking member being formed of a material crimpable over the cable to fix the locking member at a desired position on the cable.

BRIEF DESCRIPTION OF THE DRAWINGS

FIG. 5 shows a perspective view of a cable of the system of FIG. 1;

FIG. 6 shows an enlarged perspective view of a first end of the cable of FIG. 5;

FIG. 44 shows a perspective view of an first sleeve of the crimping device of FIG. 42;

FIG. 45 shows a side view of the first sleeve of FIG. 43;

FIG. 46 shows an enlarged perspective view of a distal end of the first sleeve of FIG. 43;

FIG. 47 shows a perspective view of an second sleeve of the crimping device of FIG. 42;

FIG. 48 shows a side view of the second sleeve of FIG. 47;

FIG. 49 shows an enlarged perspective view of the second sleeve of FIG. 47;

FIG. 50 shows an enlarged perspective view of the crimping device of FIG. 42, in an open configuration; and FIG. 51 shows an enlarged perspective view of the crimping device of FIG. 43, in a crimping configuration.

DETAILED DESCRIPTION

Figure 1:
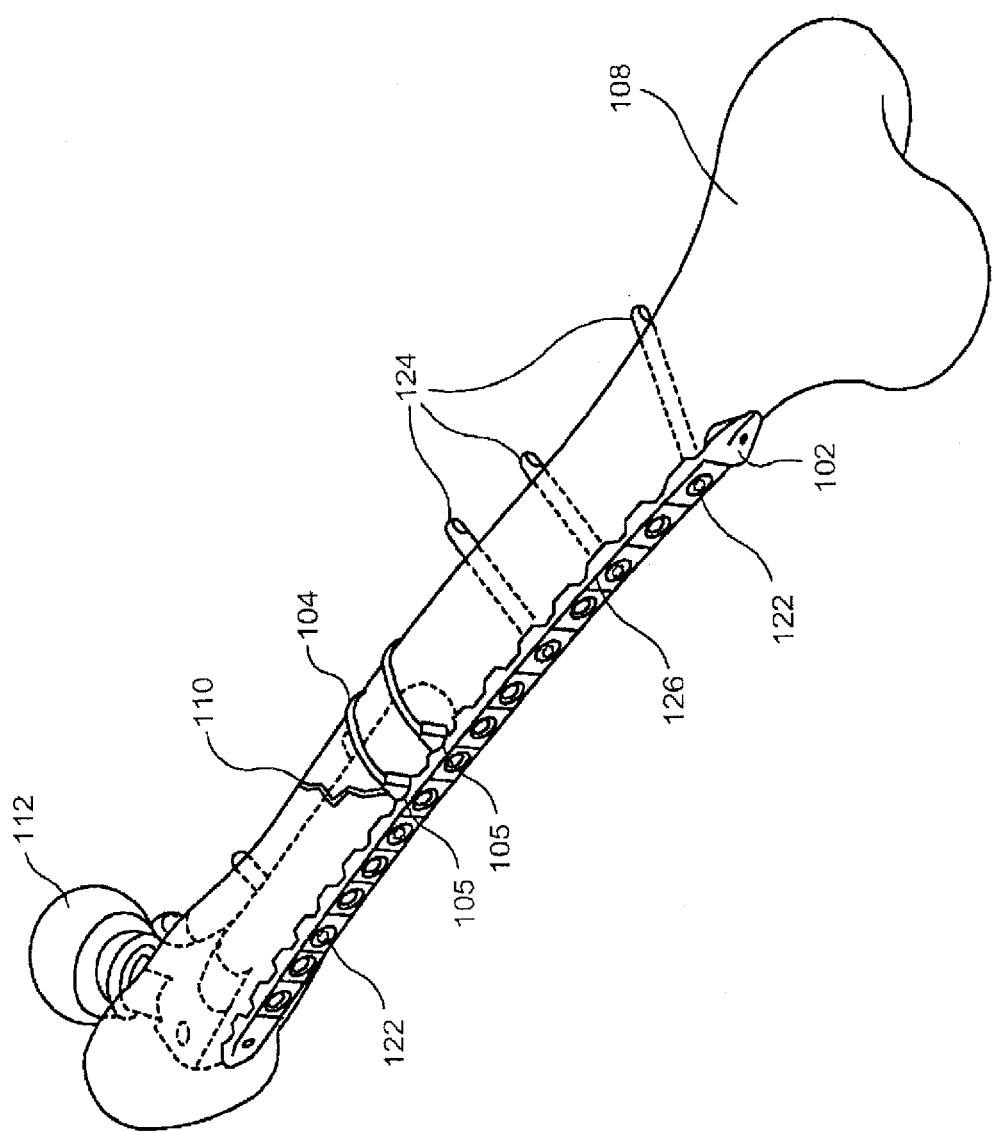
FIG. 1 shows a perspective view of a system according to an exemplary embodiment of the present invention.

The present invention may be further understood with reference to the following description and the appended drawings, wherein like elements are referred to with the same reference numerals. The present invention relates to the treatment of a bone and, in particular, to a minimally invasive treatment of a bone fracture. Exemplary embodiments of the present invention describe a system and method for treating a fracture of a bone by circling a cable around the fractured bone and crimping a crimp over the cable to hold the cable in place via a small incision through the skin. Although exemplary embodiments of the present invention specifically describe a periprosthetic fracture, it will be understood by those of skill in the art that the present invention may be used to treat other fractures as well and that this procedure is exemplary only. It will also be understood by those of skill in the art that the terms proximal and distal, as used herein, describe a direction toward (proximal) and away from (distal) a surgeon or other user.

Figure 2:
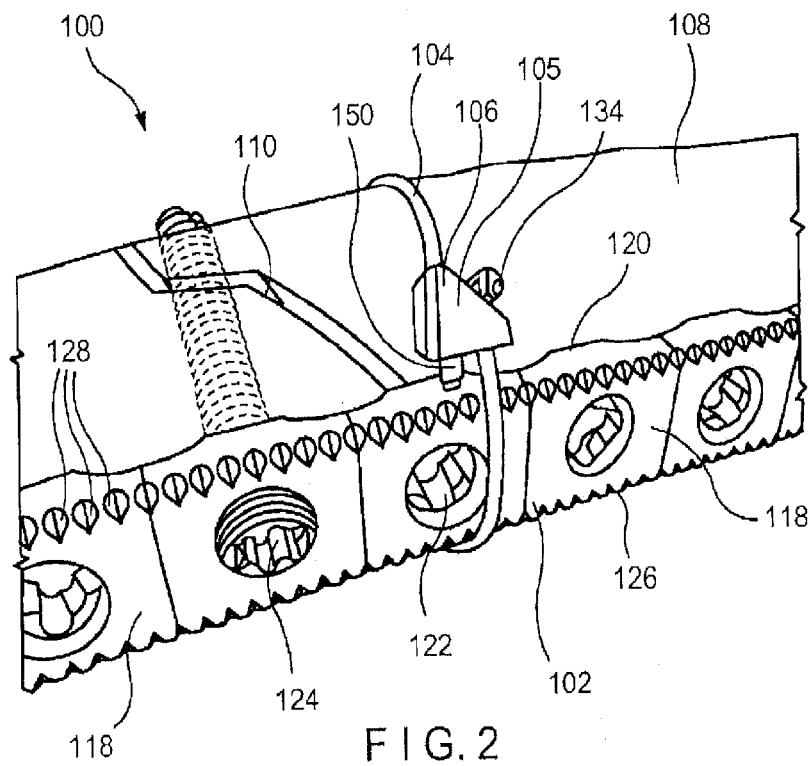
FIG. 2 shows a enlarged perspective view of a portion of the system of FIG. 1.
Figure 3:
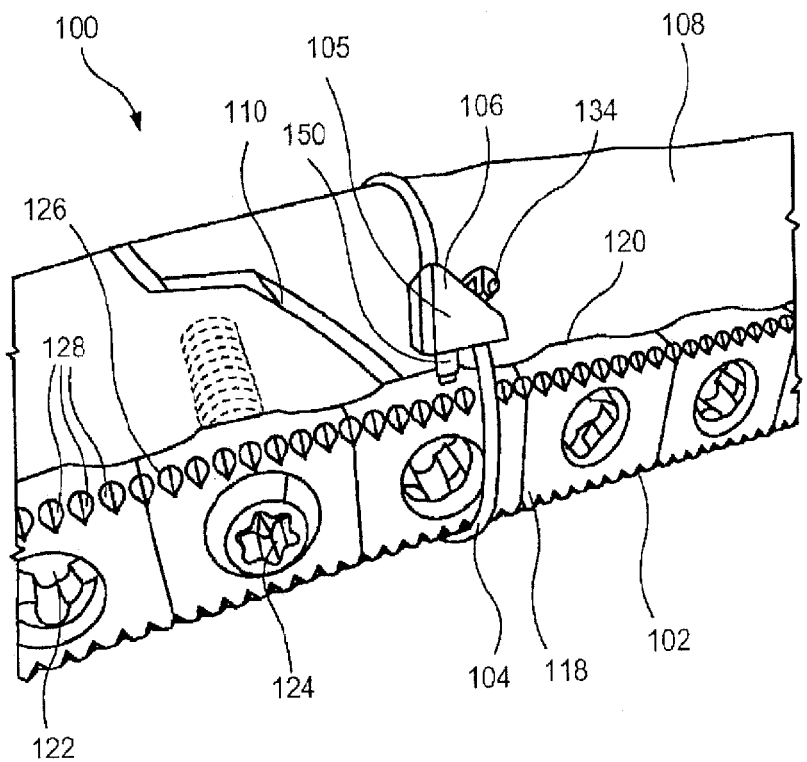
FIG. 3 shows an enlarged perspective view of a portion the system of FIG. 1.

As shown in FIGS. 1-14, a system 100 according to an exemplary embodiment of the present invention comprises a plate 102 positionable along a bone 108, a cable 104 that circles the plate 102 and the bone 108 and a crimp 105 that fixes the cable 104 at a desired tension about the plate 102 and the bone 108. As shown in FIGS. 1-3, the plate 102 may be positioned along a length of the bone 108, which may include a prosthesis 112, to provide stability to a fracture 110 of the bone 108. The cable 104 may be circled around both the plate 102 and/or the bone 108 to fix the fracture 110. The crimp 105 further comprises a cable block 106 that receives a portion of the cable 104 therethrough and a deformable member 150 that may be positioned adjacent the cable block 106 to be crimped over the cable, fixing the cable 104 about the bone 108 at a desired position and tension.

Figure 4:
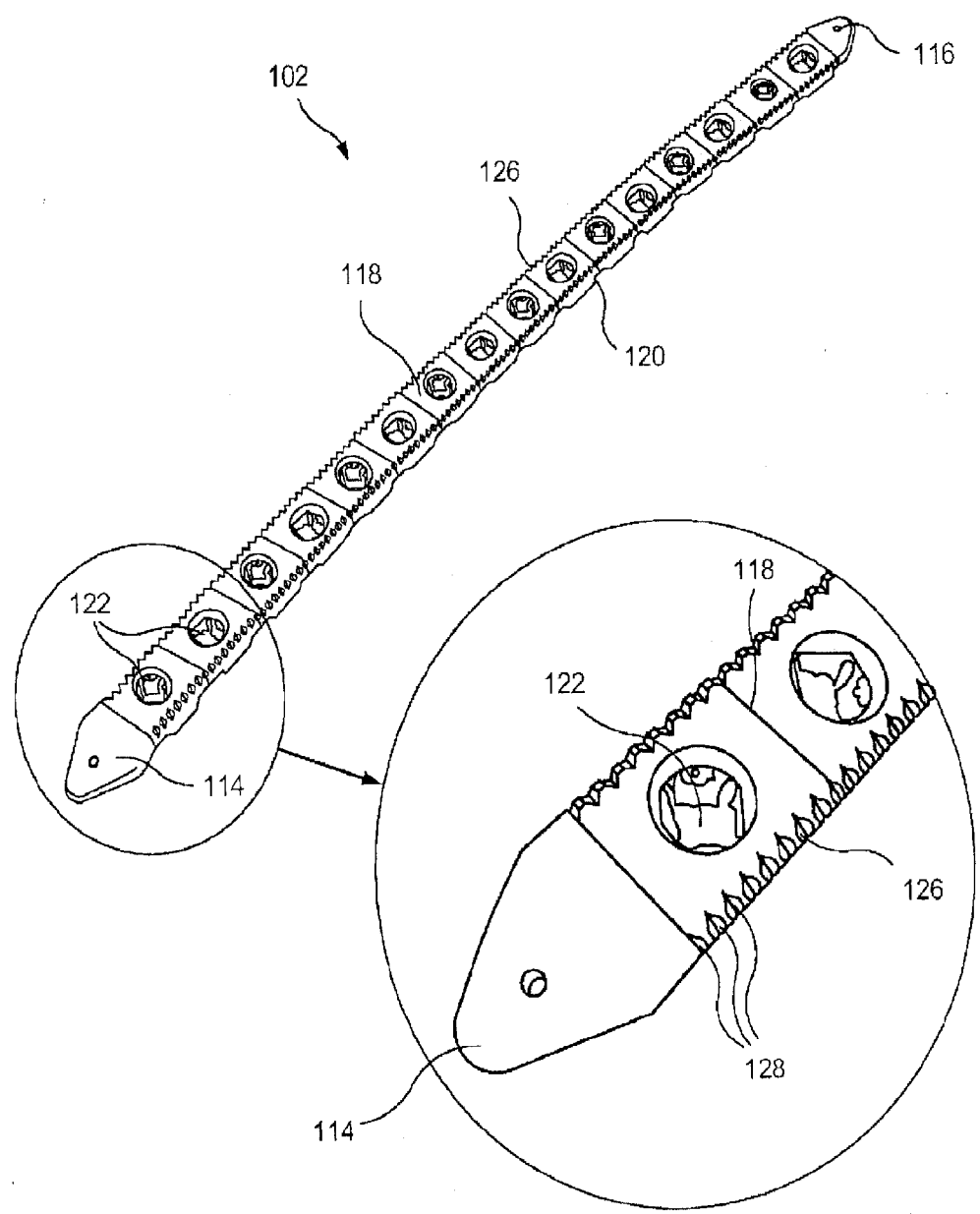
FIG. 4 shows a perspective view of a bone plate of the system of FIG. 1.
Figure 7:
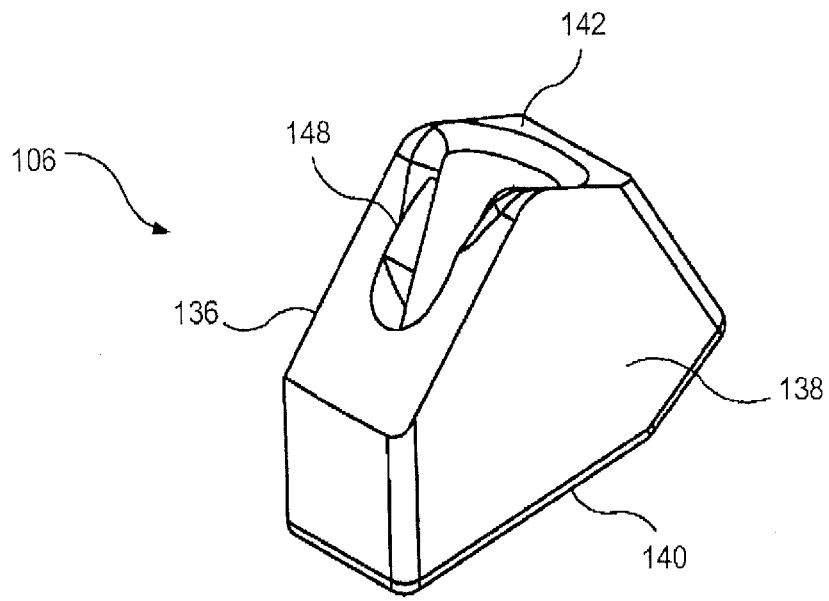
FIG. 7 shows a top perspective view of a cable block of the system of FIG. 1.
Figure 8:
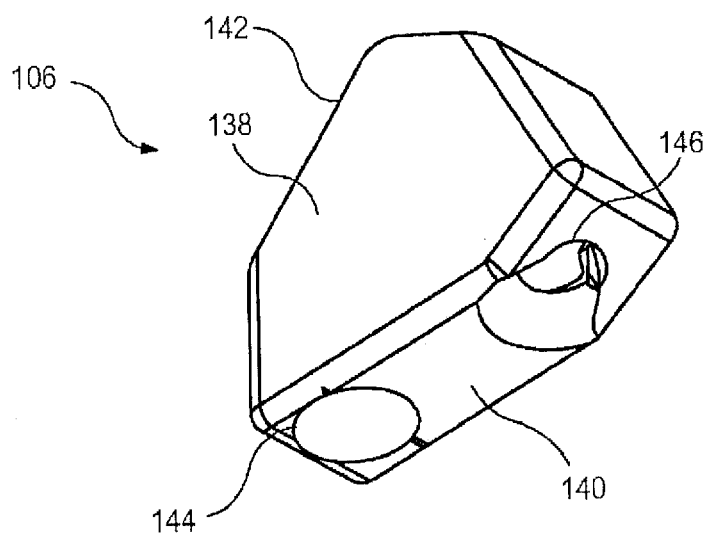
FIG. 8 shows a bottom perspective view of the cable block of FIG. 7.
Figure 9:
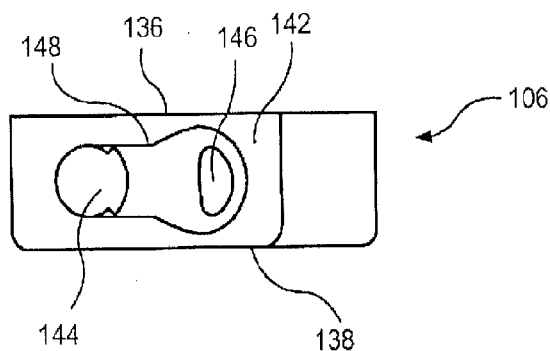
FIG. 9 shows a top plan view of the cable block of FIG. 7.
Figure 10:
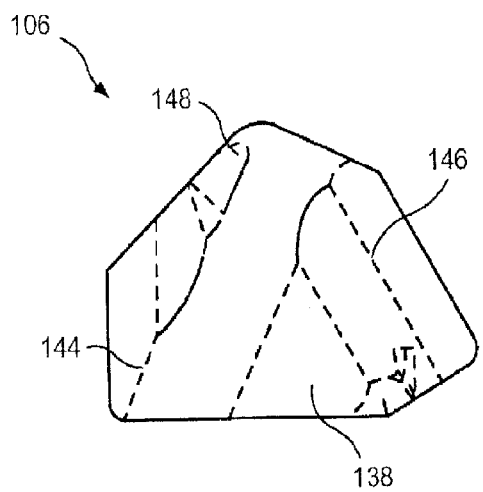
FIG. 10 shows a side view of the cable block of FIG. 7.
Figure 12:
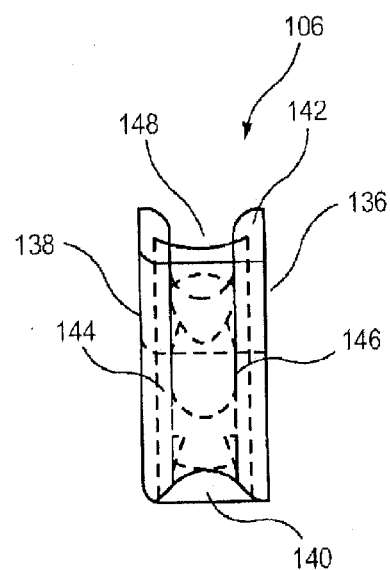
FIG. 12 shows a bottom plan view of the cable block of FIG. 7.
Figure 11:
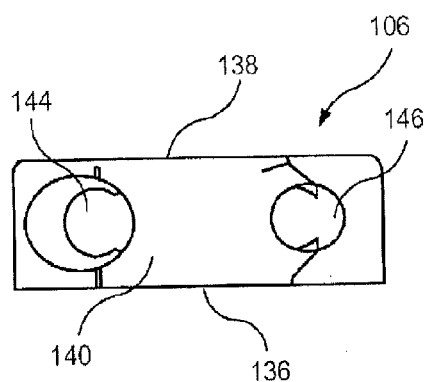
FIG. 11 shows another side view of the cable block of FIG. 7.

As shown in FIG. 4, the plate 102 extends longitudinally from a first end 114 to a second end 116 and includes a first surface 118 facing away from the bone 108 and a second surface 120 facing toward the bone 108. The bone plate 102 may include a plurality of openings 122 along a length thereof, each of the openings 122 being adapted and configured to receive a bone fixation element 124. The bone fixation element 124 may, for example, be a variable-angle locking screw, as shown in FIG. 2, or a non-locking screw, as shown in FIG. 3. An edge 126 of the first surface 118 includes grooves 128 along a length thereof to receive a width of the cable 104 when the cable 104 is circled around the bone 108 such that the cable 104 is prevented from sliding along the length of the plate 102.

The cable 104, as shown in FIGS. 5-6, extends longitudinally from a first end 130 to a second end 132. The first end 130 includes an enlarged end 134 that functions as a stop to prevent the first end from passing through the cable block 106 such that the cable 104 may be fixed around the bone 108. The enlarged end 134 may be substantially cylindrical, with a diameter of the enlarged end 134 being larger than a remaining length of the cable 104 which is sized to pass slidably through the cable block 106. It will be understood by those of skill in the art, however, that the enlarged end 134 may take any of a variety of shapes such as, for example, a sphere, so long as a maximum width of the enlarged end 134 is larger than a width of the remaining length of the cable 104 to prevent the end 134 from passing through an opening which slidably receives the remaining length of the cable 104.

As shown in FIGS. 7-12, the cable block 106 includes a first surface 136 and a second surface 138. The first surface 136 is shown facing the bone 108 while the second surface 138 is shown facing away from the bone 108. It will be understood by those of skill in the art, however, that the cable block 106 may also be positioned such that the first surface 136 faces away from the bone 108 while the second surface 138 faces toward the bone 108, The cable block 106 further includes a first lumen 144 and a second lumen 146 extending therethrough from a proximal end 140 to a distal end 142, substantially parallel to the first and second surfaces 136, 138. The first and second lumens 144, 146 are angled relative to one another such that they intersect adjacent to the distal end 142. The cable block 106 further includes a slot 148 extending into the surface of the distal end 142 connecting the first and the second lumens 144, 146, The slot 148 extends proximally into the distal end 142 across the gap between the first and second lumens 144, 146 with a width of the slot 148 being approximately equal to a diameter of the second lumen 146. That is, a width of the slot 148 is selected to permit the passage therethrough of the cable 104 but not to permit the passage of the enlarged end 134 thereof. Thus, the first and second lumens 144, 146 open to the distal end 142 via a single opening defined by the the distal ends of the first and second lumens 144, 146 and the slot 148 extending therebetween.

The first lumen 144 is sized and shaped to accommodate the cable 104, including the enlarged end 134, therethrough. The second lumen 146 is sized and shaped to allow only the remaining length of the cable 104, excluding the enlarged end 134, to pass therethrough. The slot 148 includes a first portion aligned with the first lumen sized and shaped to permit the enlarged end 134 to pass therethrough and a second part extending laterally from the first part toward the second lumen 146 with a width substantially equal to a diameter of the second lumen 146. Thus, the enlarged end 134 may pass only through the first part of the slot 148. As described below, in a locked position, the enlarged end will be displaced laterally to abut the second part of the slot 148 preventing the enlarged end 134 from passing back through the first lumen 144.

Figure 13:
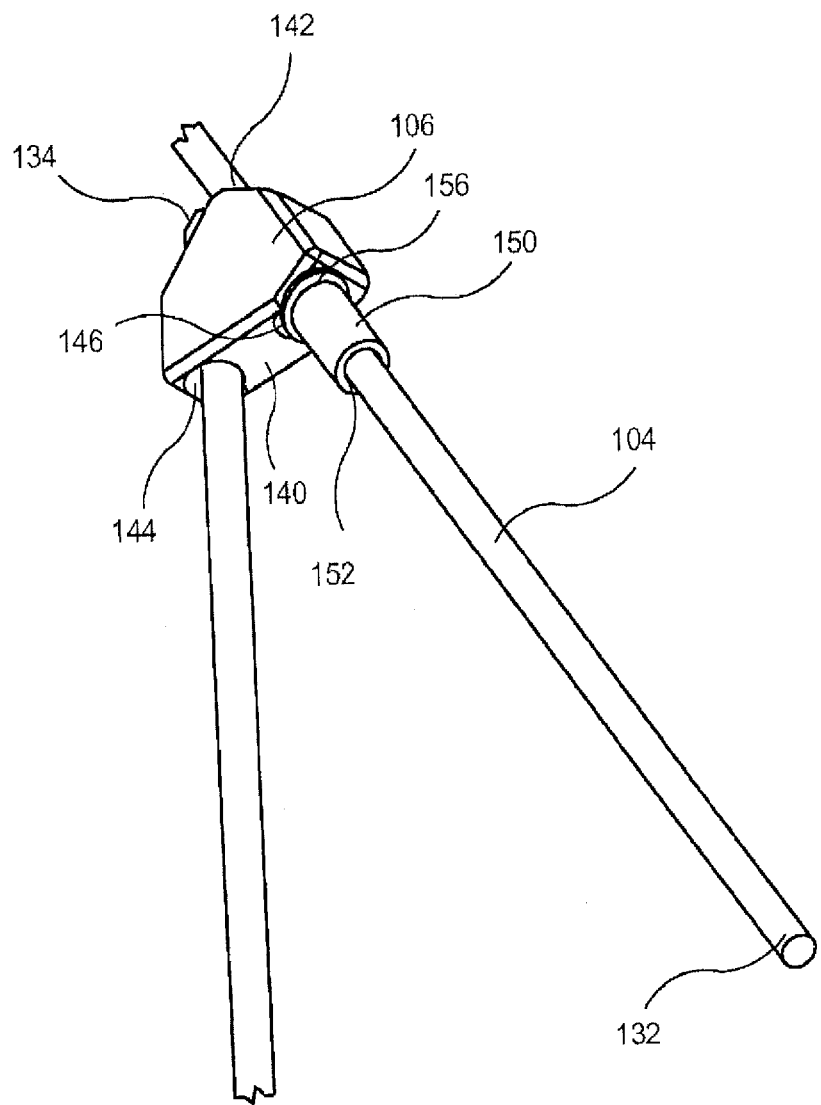
FIG. 13 shows a perspective view of the cable and the crimp of the system of FIG. 1.
Figure 14:
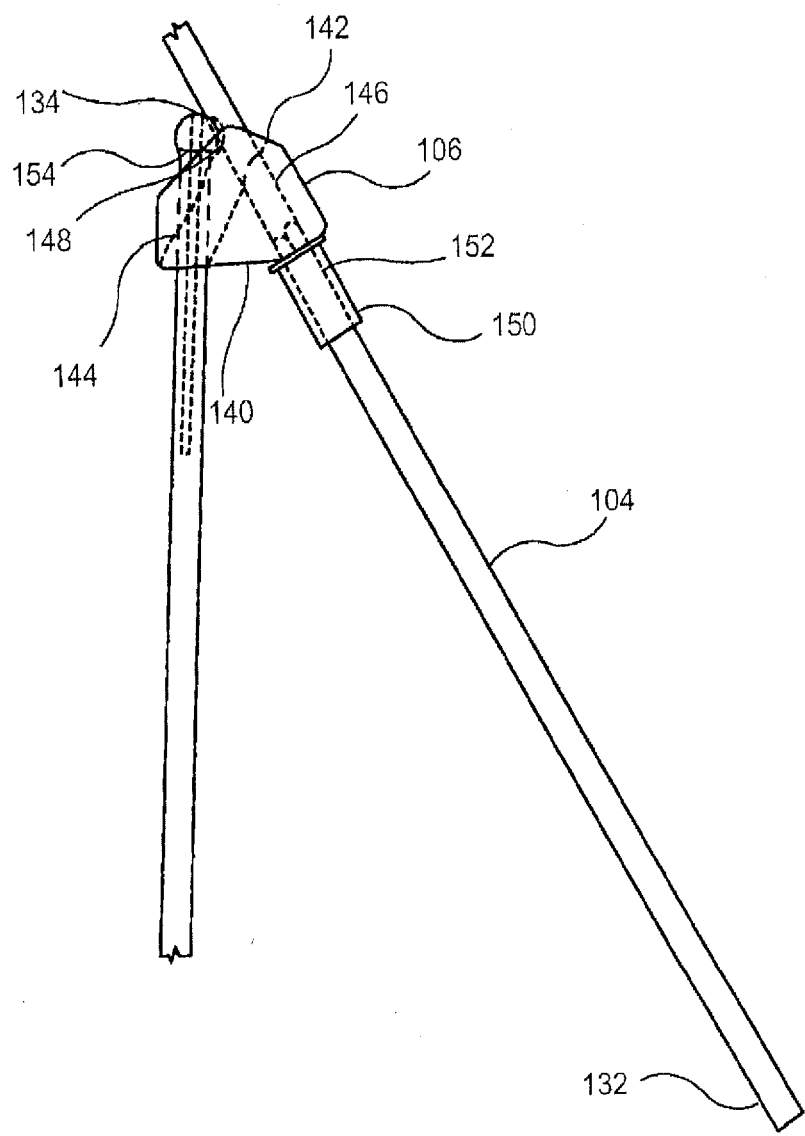
FIG. 14 shows a side view of the cable and the crimp of the system of FIG. 1.

As shown in FIGS. 13-14, the cable block 106 may be used in conjunction with the deformable member 150 to crimp the cable 104 over the bone 108. The deformable member 150 may be a short, substantially tubular member extending from a proximal end 158 to a distal end 156 and including a channel 152 extending therethrough sized and shaped to slidably receive the cable 104 therein. In use, the deformable member 150 is positioned adjacent an opening of the second lumen 146 at the proximal end 140 of the cable block 106 with the distal end 156 of the deformable member 150 abutting the proximal end 140 and crushed over the cable 104 fixing the deformable member 150 at a desired tension about the bone 108. As would be understood by those skilled in the art, the deformable member 150 is preferably formed of a deformable material such as a biocompatible metal that may be crushed over the cable 104 extending through the channel 152.

The cable 104 may be initially circled around the bone 108 and the plate 102. It will be understood by those of skill in the art that the cable 104 may be circled around the bone 108 using any of a variety of cerclage tools. Once the cable 104 has been circled as desired, the first end 130 of the cable 104, including the enlarged end 134, is inserted into the first lumen 144, entering via the proximal end 140 and extending distally past the distal end 142. The enlarged end 134 may then be moved laterally so that a proximal end 154 of the enlarged end 134 engages the second part of the slot 148 such that the enlarged end cannot pass proximally therethrough. Engagement of the enlarged end 134 with the second part of the slot 148 exposes an opening at the distal end 142 to the second lumen 146 permitting the second end 132 of the cable 104 to be inserted through the second lumen via the distal end 142 to extend proximally past the proximal end 140. The second end 132 extending past the proximal end 140 may then be threaded through the channel 152 of the deformable member 150 until the distal end 156 of the deformable member 150 abuts the proximal end 140 of the cable block 106.

The user then applies tension to the cable 104 to draw the cable 104 tightly around the bone 108 pressing the distal end 156 of the deformable member 150 is pressed against the proximal end 140 of the cable block 106. Once the desired tension has been applied to the cable 104, the user may use one of the crimping devices 200, 300, 400, as described below, to crimp the deformable member 150, crushing the deformable member 150 against the portion of the cable 104 passing therethrough and fixing the cable 104 around the bone 108 and through the cable block 106 at the desired tension.

Figure 15:
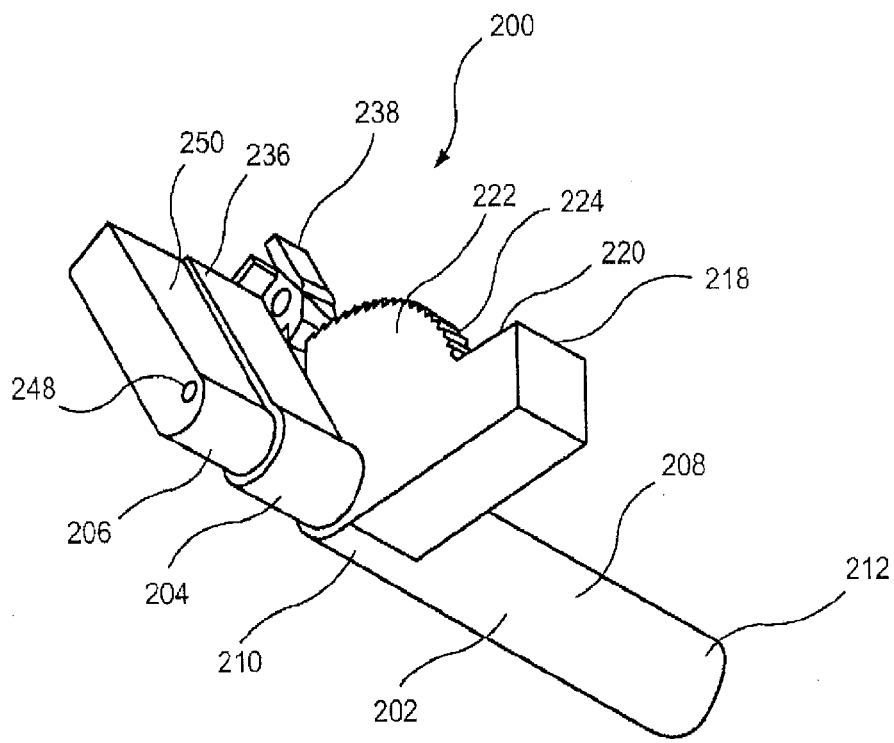
FIG. 15 shows a perspective view of a crimping device according to a first exemplary embodiment of the present invention, in an open configuration.
Figure 16:
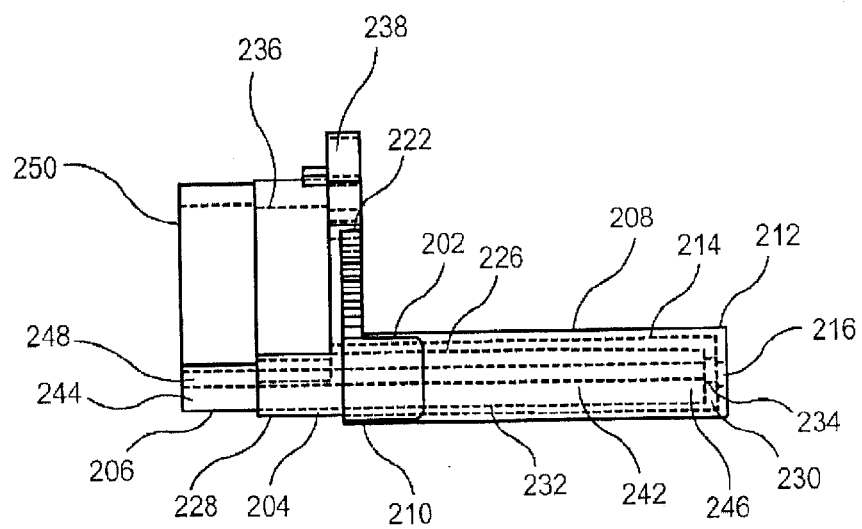
FIG. 16 shows a side view of the crimping device of FIG. 15, in the open configuration.

As shown in FIGS. 15-29, the crimping device 200 according to a first exemplary embodiment of the present invention comprises a first sleeve 202 for holding a portion of the deformable member 140, a second sleeve 204 for crimping the deformable member 150 and a third sleeve 206 for cutting the cable 104 adjacent the proximal end 158 of the deformable member 150. As shown in FIGS. 15-16, the first, second and third sleeves 202, 204, 206 are coaxially nested within one another such that each of the sleeves 202, 204, 206 is rotatable relative to the others about a longitudinal axis of the crimping device 200. The first sleeve 202 holds the deformable member 150 against the crimp 106, with the cable 104 extending therethrough, while the second and/or third sleeves 204, 206 may be moved relative to the first sleeve 202 to crimp the deformable member 150 over the cable 104 and subsequently cut the cable 104 proximally of the deformable member 150, respectively.

Figure 17:
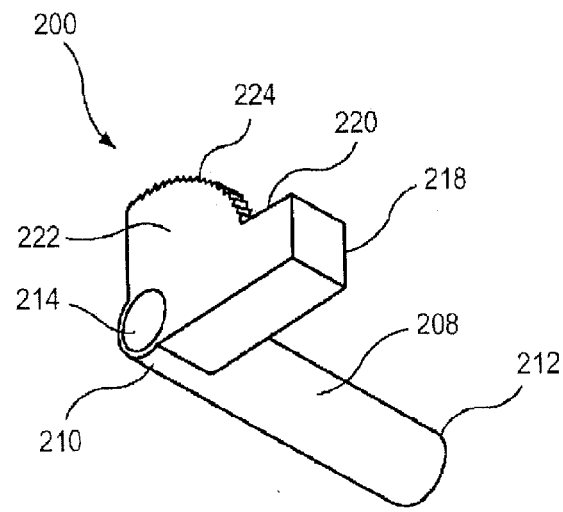
FIG. 17 shows a perspective view of a first sleeve of the crimping device of FIG. 15.
Figures 18, 19:
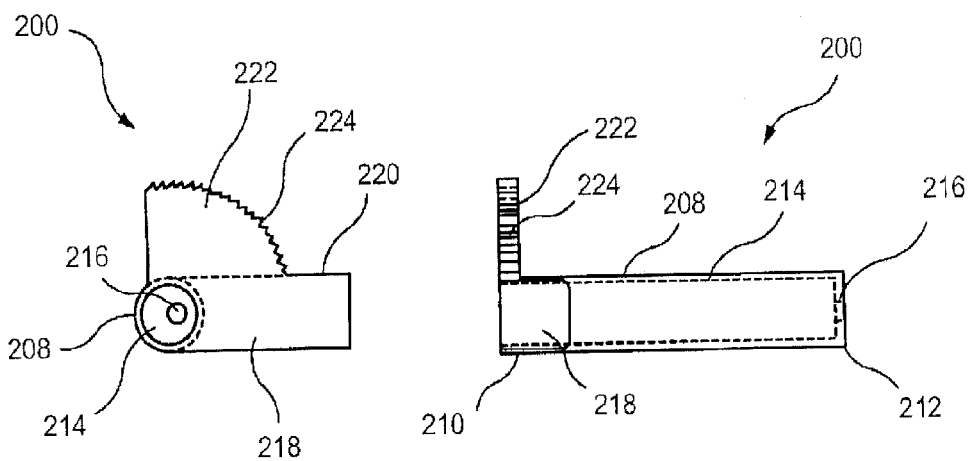
FIG. 18 shows a top view of the first sleeve of FIG. 17.
FIG. 19 shows a side view of the first sleeve of FIG. 17.

As shown in FIGS. 17-19, the first sleeve 202 includes a first longitudinal body 208 extending from a proximal end 210 to a distal end 212 and including a first lumen 214 extending therethrough sized and shaped to accommodate a second longitudinal body 226 of the second sleeve 204. A distal opening 216 of the first lumen 214 is off-center with respect to a longitudinal axis of the first longitudinal body 208. The first sleeve 202 further includes a handle 218 extending laterally from the proximal end 210 of the longitudinal body 208. Extending from a side 220 thereof is a quadrant gear wheel 222 including teeth 224 along a perimeter thereof. The gear wheel 222 extends substantially radially about the longitudinal axis of the first longitudinal body 208.

Figure 20:
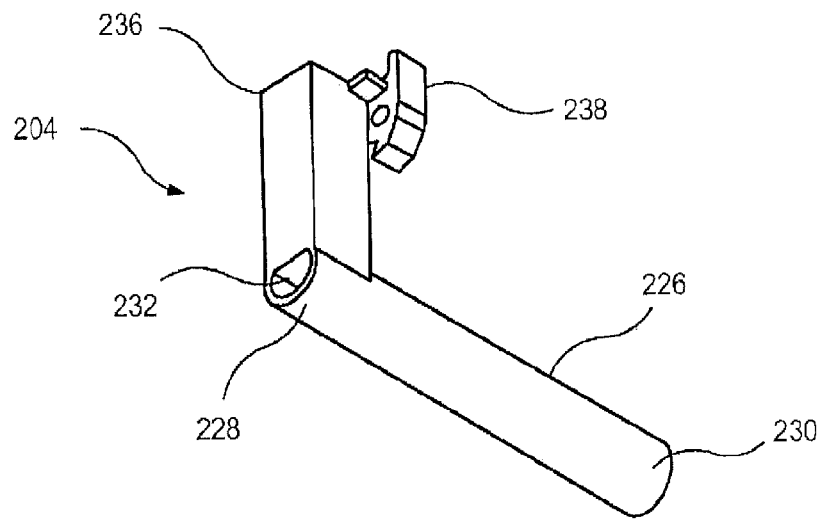
FIG. 20 shows a perspective view of a second sleeve of the crimping device of FIG. 15.
Figures 21, 22:
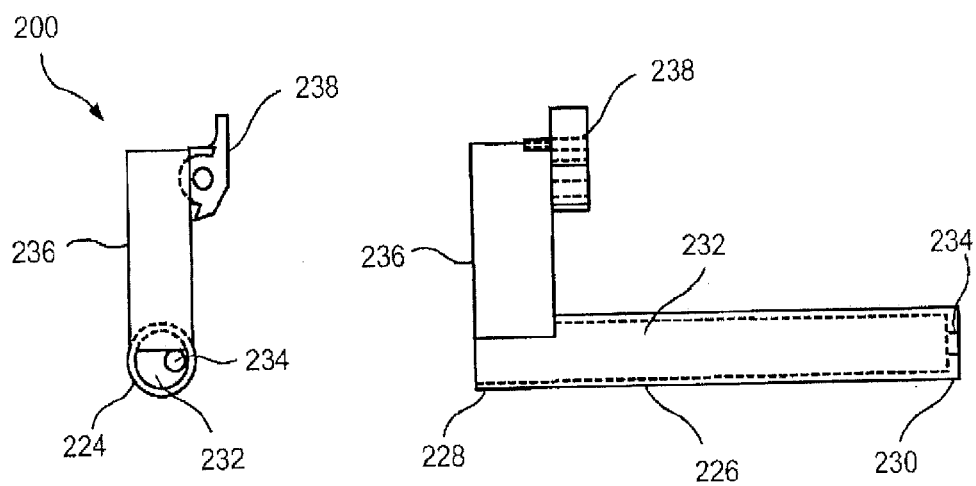
FIG. 21 shows a top view of the second sleeve of FIG. 20.
FIG. 22 shows a side view of the second sleeve of FIG. 20.

As shown in FIGS. 20-22, the second sleeve 204 includes a second longitudinal body 226 extending from a proximal end 228 to a distal end 230 with a second lumen 232 extending therethrough sized and shaped to receive a third longitudinal body 242 of a third sleeve 206. The second longitudinal body 226 is sized and shaped to be received within the first lumen 214 of the first sleeve 202. A distal opening 234 of the second lumen 232 is off-center of a longitudinal axis of the second longitudinal body 226. The second sleeve 204 further includes a handle 236 and a ratchet pawl 238. The handle 236 extends laterally of the proximal end 228 while the ratchet pawl 238 is attached to a distal surface 240 of the handle 236. A length of the second longitudinal body 226 is longer than a length of the longitudinal body 208 of the first sleeve such that when the second longitudinal body 226 is inserted into the first lumen 214, the distal end 230 abuts the distal end 212 of the first longitudinal body 208 and the handle 236 of the second sleeve 204 abuts the handle 218 of the first sleeve 202 such that the ratchet pawl 238 engages the teeth 224 of the quadrant wheel 222. Thus, it will be understood by those of skill in the art that the first sleeve 202 and the second sleeve 204 are rotatable relative to one another about a longitudinal axis of the crimping device 200. However, engagement between the ratchet pawl 238 and the teeth 224 of the quadrant wheel prevent the first and second sleeves 202, 204 from rotating uncontrollably relative to one another.

Figure 23:
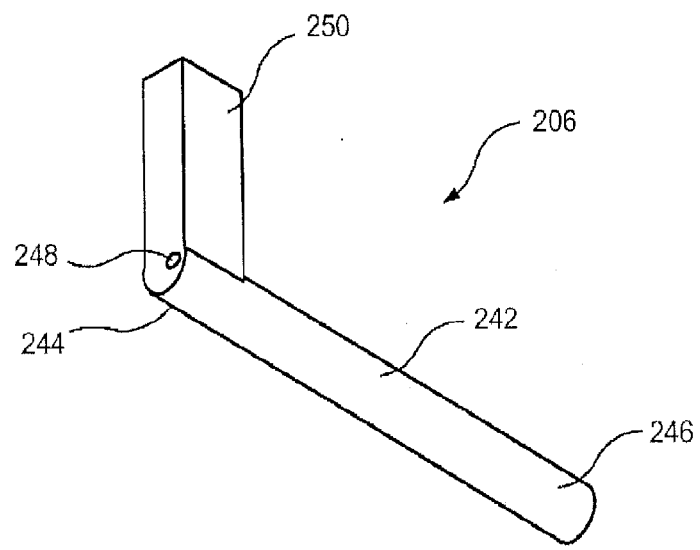
FIG. 23 shows a perspective view of a third sleeve of the crimping device of FIG. 15.
Figures 24, 25:
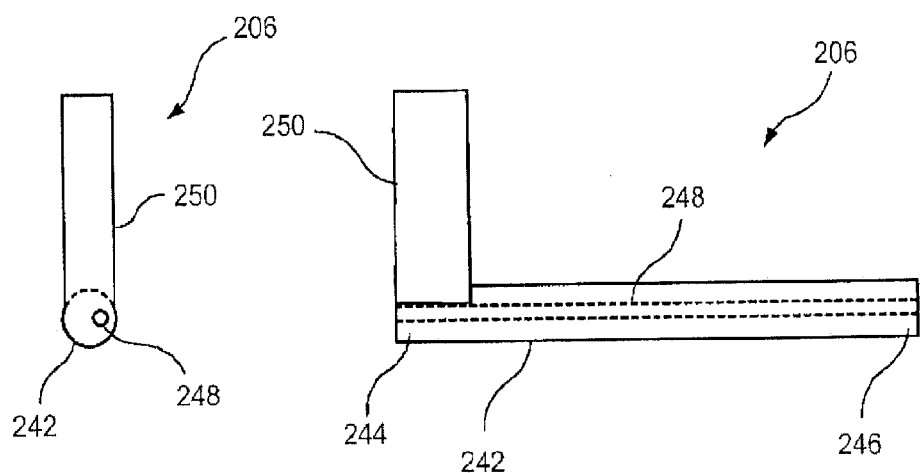
FIG. 24 shows a top view of the third sleeve of FIG. 23.
FIG. 25 shows a side view of the third sleeve of FIG. 23.

As shown in FIGS. 23-25, the third sleeve 206 includes a third longitudinal body 242 extending from a proximal end 244 to a distal end 246 and including a third lumen 248 extending therethrough sized and shaped to receive the deformable member 150 and the cable 104 therein. The third longitudinal body 242 may be sized and shaped to be received within the second lumen 232. The third lumen 248 may be off-center of a longitudinal axis of the third longitudinal body 242. The third sleeve 206 further includes a handle 250 extending laterally from the proximal end 244 of the third longitudinal body 242. A length of the third longitudinal body 242 is longer than a length of the second longitudinal body 226 such that when the third longitudinal body 242 is received within the second lumen 232, the distal end 246 abuts the distal end 230 of the second sleeve 204 and the handle 250 abut the handle 236 of the second sleeve 204.

Figure 26:
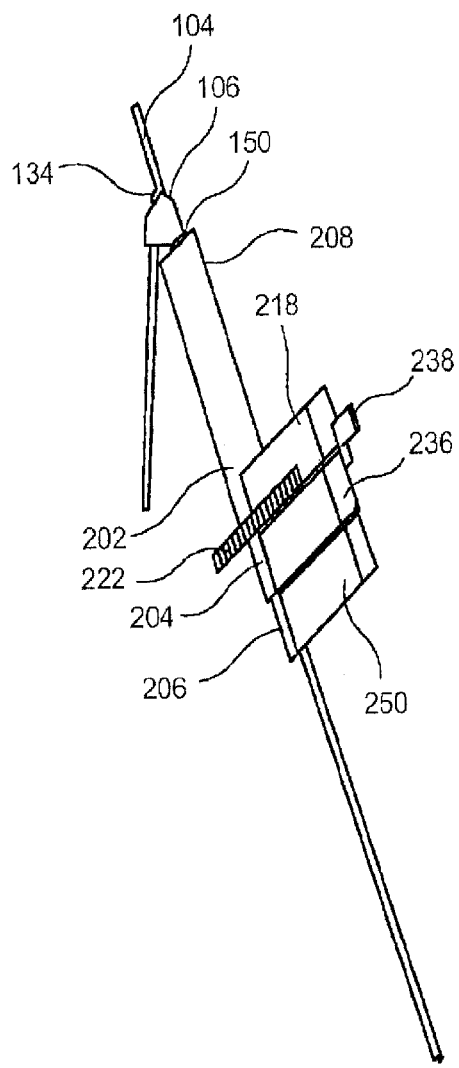
FIG. 26 shows a side view of the crimping device of FIG. 15, in a crimping configuration.
Figure 27:
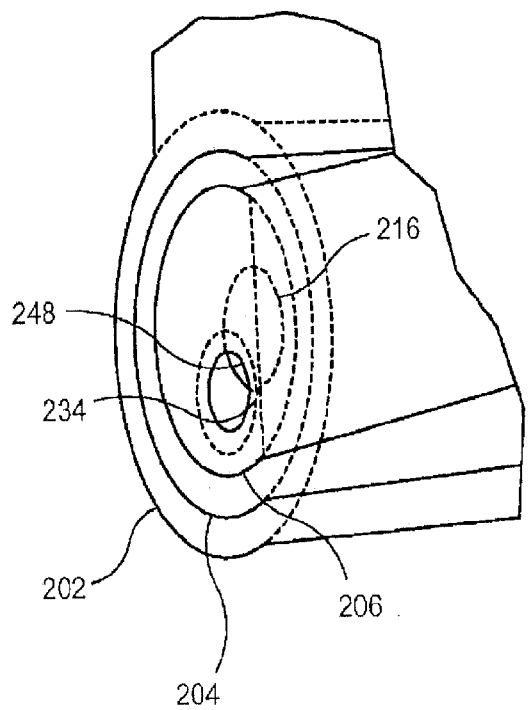
FIG. 27 shows a perspective view of a distal end of the crimping device in the crimping configuration of FIG. 26.

FIGS. 15-16 show the crimping device 200 in an open configuration in which the first, second and third sleeves 202, 204, 206 are nested as described above and the off center distal openings 216, 234 of the first sleeve 202 and the second sleeve 204, respectively are aligned along with the off-center lumen 248 of the third sleeve 206 to allow the deformable member 150, which includes the cable 104 passing therethrough, to be received therein. In the open configuration, the handle 218 of the first sleeve 202 may be substantially perpendicular to the handles 236, 250 of the second and third sleeves 204, 206, respectively. After tension is applied to the cable 104, the crimping device 200 is moved into a crimping configuration, as shown in FIGS. 26-27. In the crimping configuration, the handles 236, 250 of the crimping and third sleeves 204, 206 may be rotated relative to the first sleeve 202 such that the handles 236, 250 are substantially aligned with the handle 218 of the first sleeve 202 and the distal opening 234 and the lumen 248 of the crimping and third sleeves 204, 206 are no longer aligned with the distal opening 216 of the first sleeve 202, thereby crimping the deformable member 150 over the cable 104 and fixing the cable 104 relative to the cable block 106 and the deformable member 150.

Figure 28:
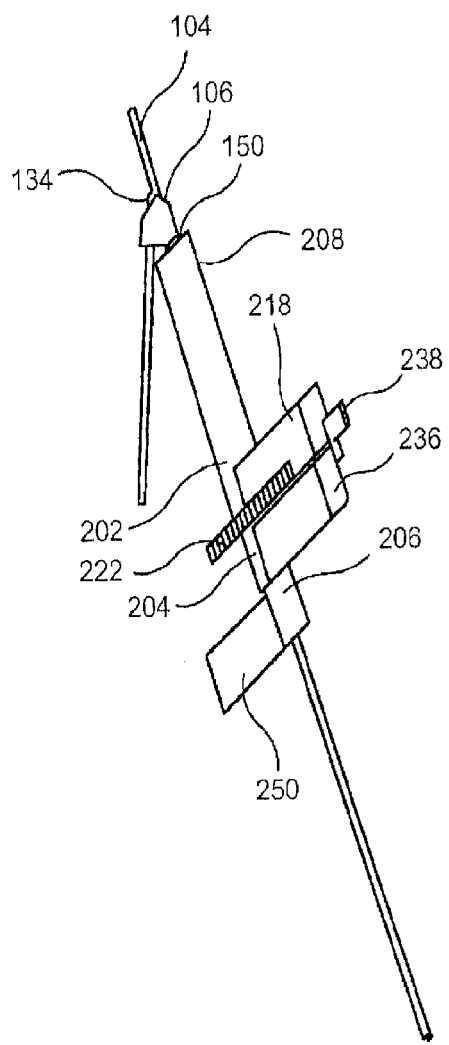
FIG. 28 shows a side view of the crimping device of FIG. 16, in a cutting configuration.
Figure 29:
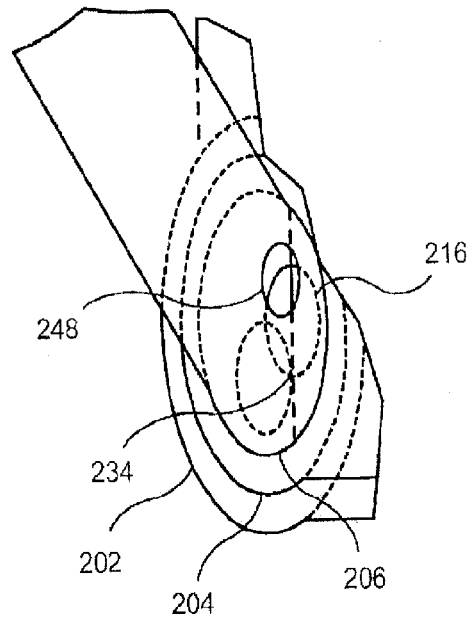
FIG. 29 shows a perspective view of the distal end of the crimping device in the cutting configuration of FIG. 28.

Once the deformable member 150 has been crimped by the crimping device 200 to fix the cable 104 about the bone 108, the crimping device 200 may be moved to a cutting configuration, as shown in FIGS. 28-29, to cut the cable 104 adjacent the proximal end 158 of the deformable member 150 such that an excess length of the cable 104 is removed. In the cutting configuration, the third sleeve 206 is rotated relative to the first sleeve 202 and the second sleeve 204 such that the handle 250 is substantially radially opposed to the handles 218, 236 of the first and second sleeves 202, 204, respectively. The third lumen 248 is completely off-set from both the distal openings 216, 234 such that the cable 104 is cut flush to the deformable member 150. Once the deformable member 150 has been crimped and the cable 104 cut, the crimping device 200 may be removed from the body, along with the excess cable 104.

Figure 30:
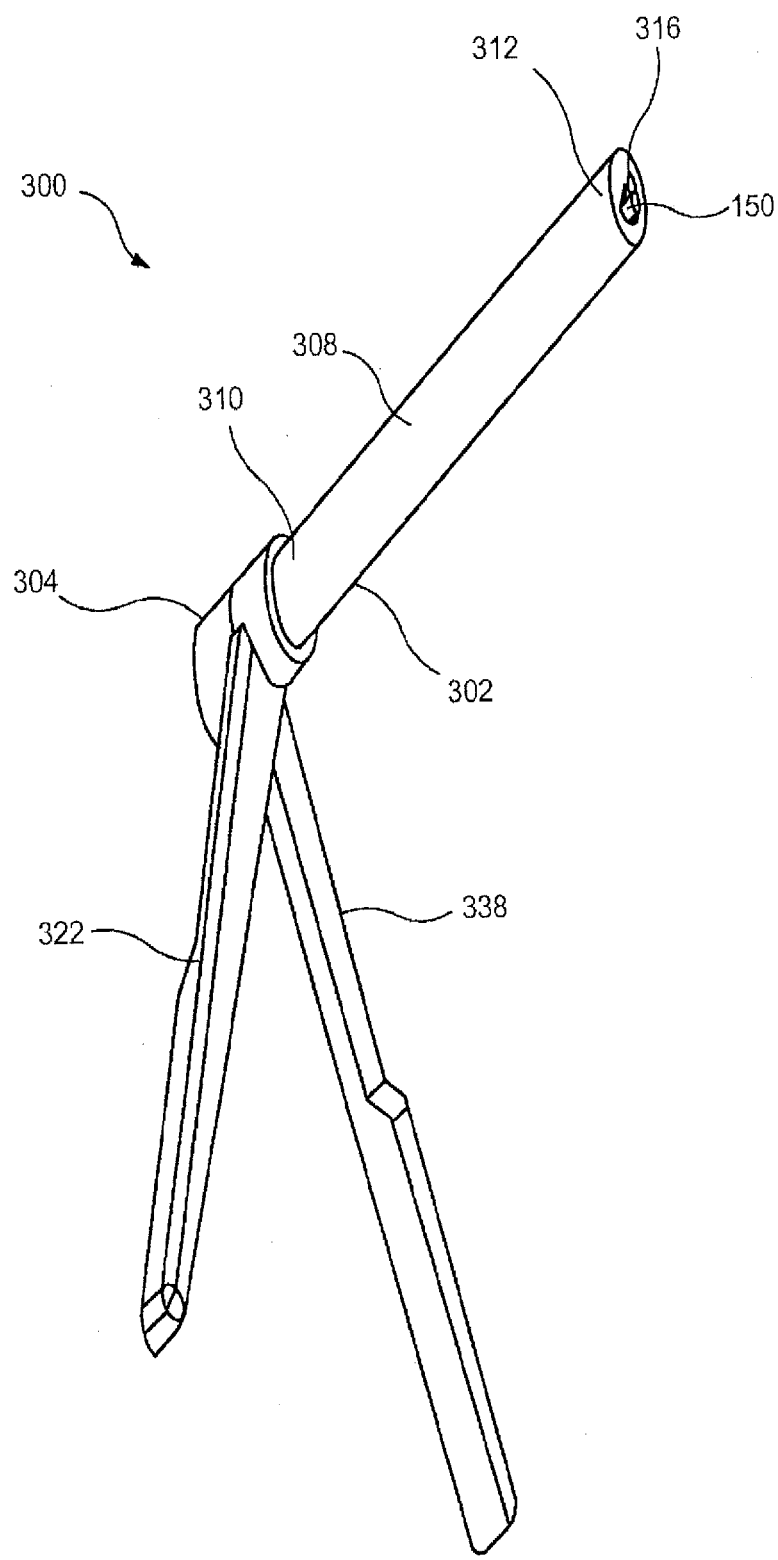
FIG. 30 shows a perspective view of a crimping device according to a second exemplary embodiment of the present invention, in an open configuration.
Figure 31:
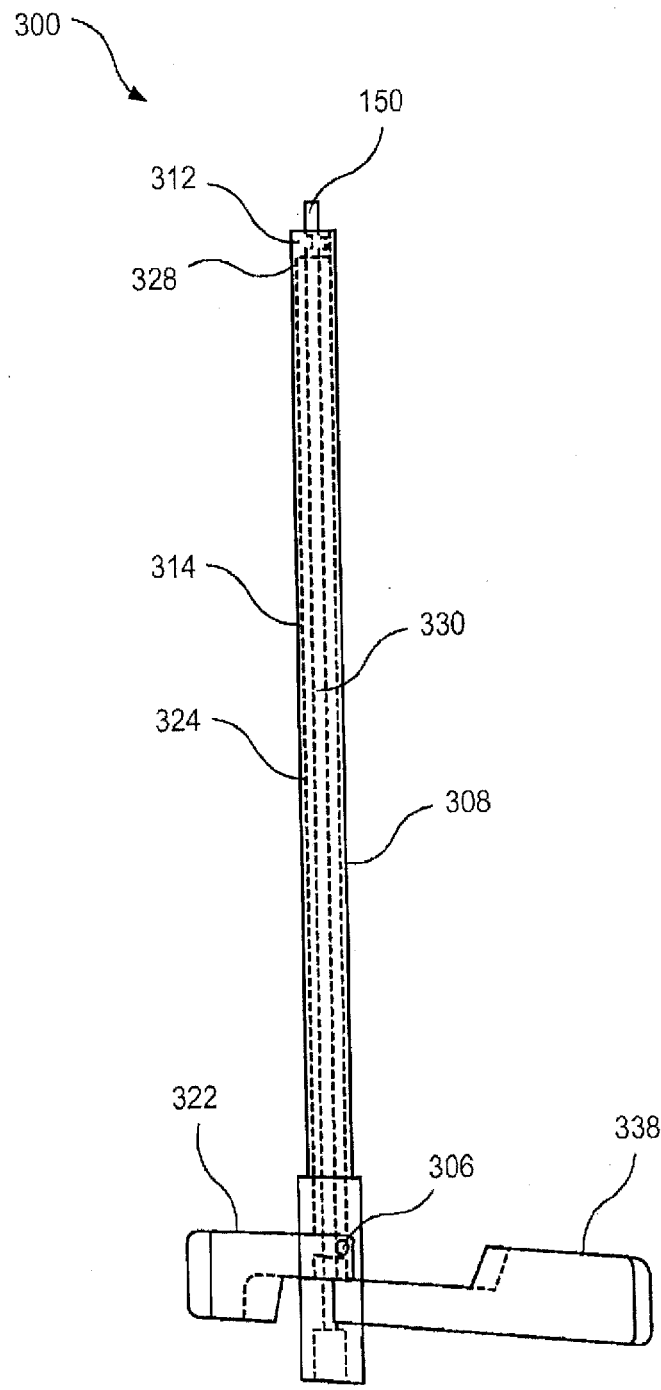
FIG. 31 shows a side view of the crimping device of FIG. 30, in the open configuration.

Similarly to the crimping device 200, a crimping device 300, as shown in FIGS. 30-41, may be used to crimp the deformable member 150 of the system 100, as described above, over the cable 104. As shown in FIGS. 30-31, the crimping device 300 comprises a first sleeve 302 and an second sleeve 304 substantially housed within the first sleeve 302. The first and second sleeves 302, 304 are rotatable relative to one another about longitudinal axes thereof, between an open configuration and a crimping configuration, in which first and second crimping surfaces 318, 336 of the first and second sleeves 302, 304, respectively, are move toward one another to crimp the deformable member 150 therebetween, over the cable 104. The first and second sleeves 302, 304 may be coupled to one another via a pin 306, adapted and configured to permit the first and second sleeves 302, 304, respectively, to rotate relative to one another while preventing the first and second sleeves 302, 304 from moving longitudinally relative to one another. The crimping device 300, however, does not include a cutting mechanism. Thus, it will be understood by those of skill in the art that any known separate cutting device may be utilized when using the crimping device 300 to cut the cable 104 as desired.

Figure 32:
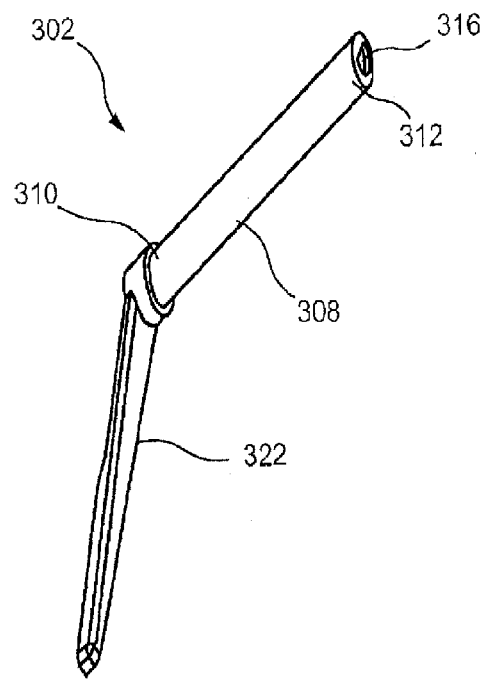
FIG. 32 shows a perspective view of an first sleeve of the crimping device of FIG. 30.
Figures 33, 34:
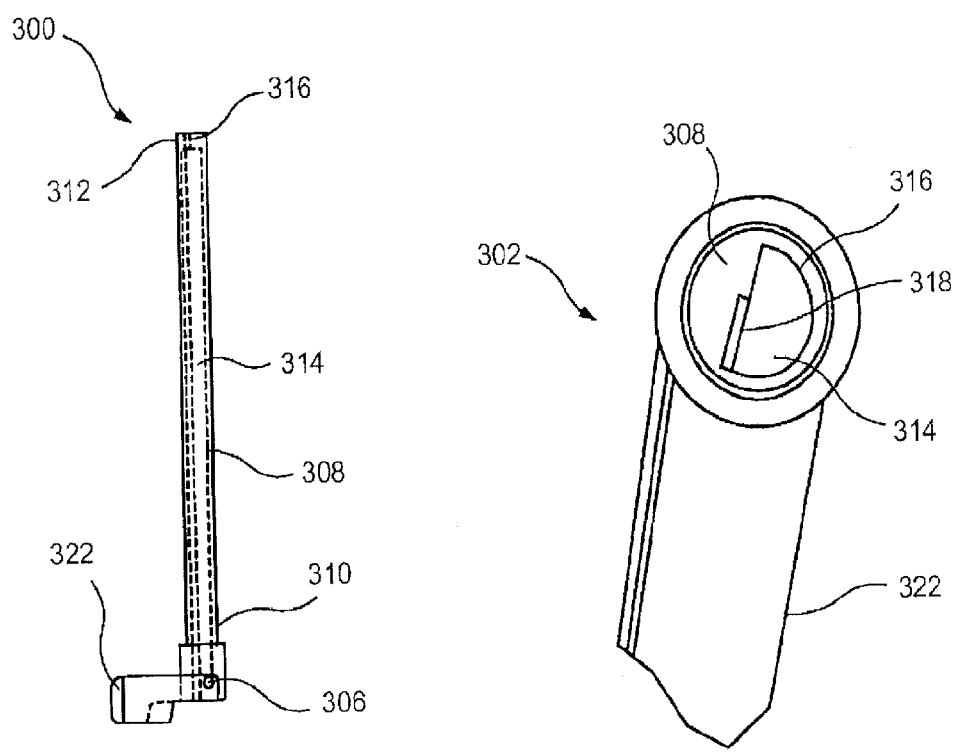
FIG. 33 shows a side view of the first sleeve of FIG. 32.
FIG. 34 shows a plan view of a distal end of the first sleeve of FIG. 32.

As shown in FIGS. 32-34, the first sleeve 302 includes a first longitudinal body 308 extending from a proximal end 310 to a distal end 312 and including a first lumen 314 extending therethrough. The first lumen 314 may be sized and shaped to receive a second longitudinal body 324 of the second sleeve 304. A distal opening 316 of the first lumen 314 may be substantially semi-circular and sized to permit the deformable member 150, along with the cable 104 passing therethrough, to be received therein. The distal opening 316 includes the first crimping edge 318 tapered relative to a remaining portion of the distal opening 316. The proximal end 310 of the first longitudinal body 308 further includes a lateral hole 320 for receiving the pin 306. It will be understood by those of skill in the art that the pin 306 and the lateral hole 320 may be correspondingly threaded such that the pin 306 and the lateral hole 320 threadedly engage one another, preventing the pin 306 from coming loose during use of the crimping device 300. The first sleeve 302 may further include a handle 322 extending laterally from the proximal end 310.

Figure 35:
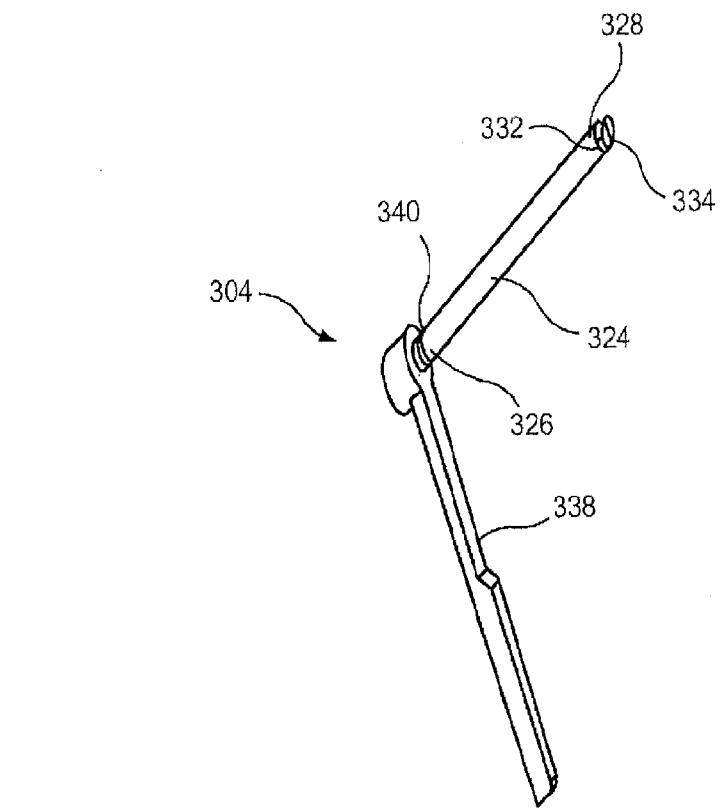
FIG. 35 shows a perspective view of an second sleeve of the crimping device of FIG. 30.
Figure 36:
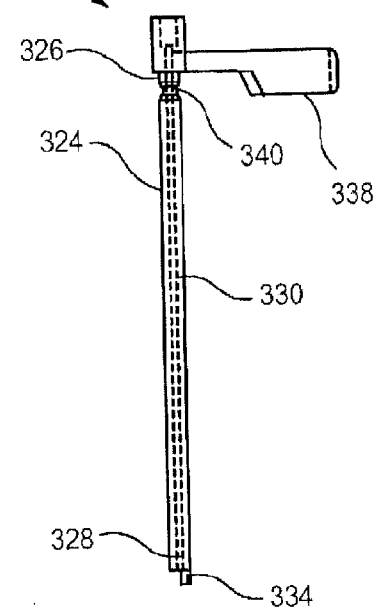
FIG. 36 shows a side view of the second sleeve of FIG. 35.
Figure 37:
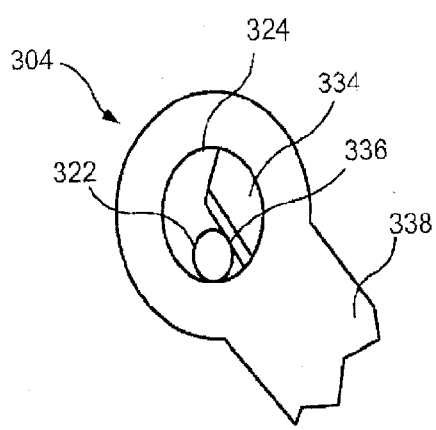
FIG. 37 shows a plan view of a distal end of the second sleeve of FIG. 35.

As shown in FIGS. 35-37, the second sleeve 304 includes the second longitudinal body 324, which extends from a proximal end 326 to a distal end 328 and includes a second lumen 330 extending therethrough. The second longitudinal body 324 is sized and shaped to be received within the first lumen 314. The second lumen 330 is sized and shaped to accommodate the cable 104 and the deformable member 150 therethrough and is off-set from a longitudinal axis of the second sleeve 304 such that a distal opening 332 of the second lumen 330 is not co-axial with the longitudinal axis of the second sleeve 304. Proximate the distal opening 332, the second sleeve 304 further includes a protrusion 334 extending distally from the distal end 328. The protrusion 334 may be formed as a portion of a semi-circle such that the protrusion 334 is receivable through the distal opening 316 of the first lumen 314, along with the deformable member 150. The protrusion 334 includes the second crimping edge 336 on a side thereof facing the distal opening 332 of the second lumen 330, which may be tapered relative to a remaining portion of the protrusion 334, to facilitate crimping of the deformable member 150. The second sleeve 304 may further include a handle 338 extending laterally from the proximal end 326 of the second longitudinal body 324.

The second sleeve 304 further includes a groove 340 for receiving a portion of the pin 306, the groove 304 being proximate the handle 338 at the proximal end 326 of the second longitudinal body 324 and extending around at least a portion of a circumference of the second longitudinal body 324 such that when the second longitudinal body 324 is inserted into the first lumen 314, the lateral hole 320 and the groove 340 are longitudinally aligned. Thus, it will be understood by those of skill in the art that when the first sleeve 302 and the second sleeve 304 are coupled via the pin 306, the first and second sleeves 302, 304 are rotatable relative to one another but prevented from moving longitudinally relative to one another. A length of the second longitudinal body 324 is preferably selected so that when the second longitudinal body 324 is inserted into the first lumen 314 of the first sleeve 302, the distal end 328 of the second longitudinal body 324 abuts the distal end 312 of the first sleeve 302 and the handle 338 of the second sleeve 304 abuts the handle 322 of the first sleeve 302.

Figure 38:
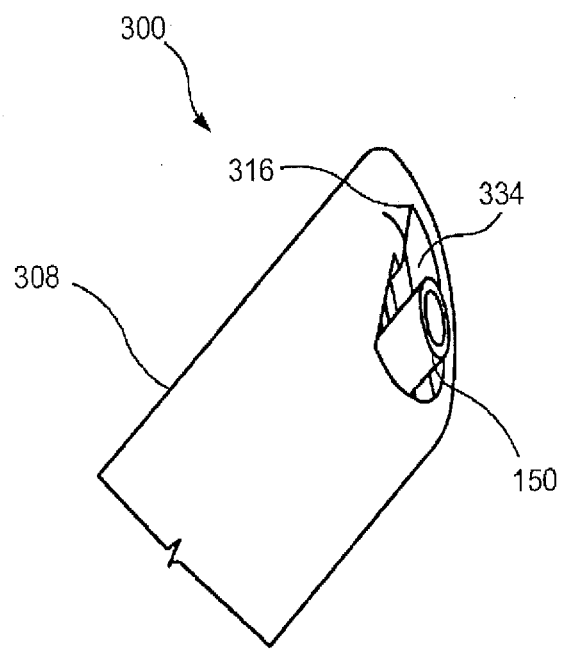
FIG. 38 shows a perspective view of a distal end of the crimping device of FIG. 30, in the open configuration.
Figure 39:
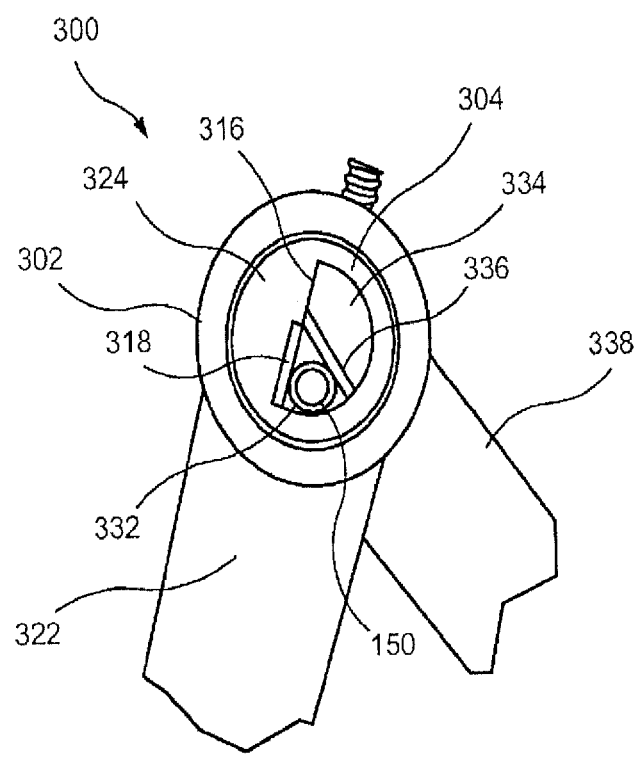
FIG. 39 shows a plan view of the distal end of the crimping device in the open configuration of FIG. 38.

In the open configuration, as shown in FIGS. 38-39, the semi-circular distal opening 316 of the first sleeve 304 is substantially aligned with the protrusion 334 and the distal opening 332 of the lumen 330 of the second sleeve so that the protrusion 334 extends through the distal opening 316 of the first sleeve 304 and the distal opening 332 of the second sleeve 304 is fully exposed to receive the deformable member 150 therein. The first crimping edge 318 of the first sleeve 302 and the second crimping edge 336 of the second sleeve 304 are positioned on substantially opposite sides of the distal opening 332. The handles 322, 338 of the first and second sleeves 302, 304, respectively, may be angled relative to one another. In the open configuration, the deformable member 150 is inserted into the distal openings 316, 332 and the portion of the cable 104 passing proximally through the deformable member 150 extends proximally through the lumen 330.

Figure 40:
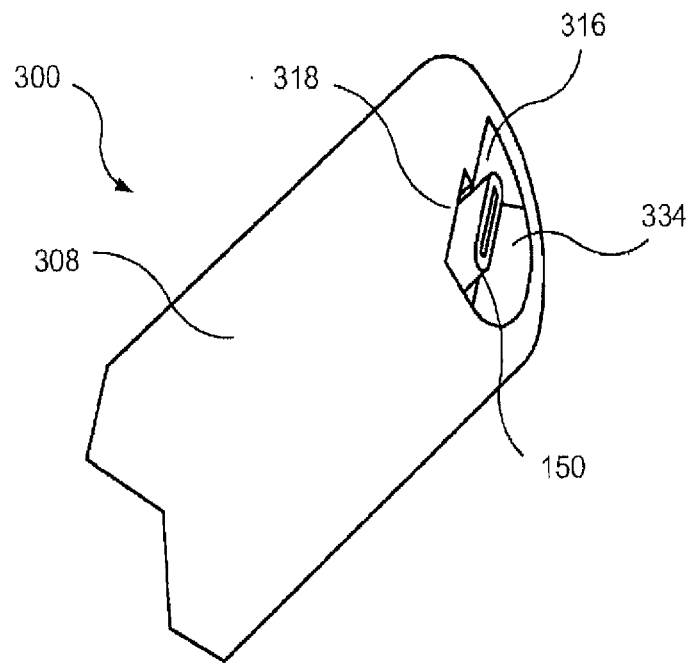
FIG. 40 shows a perspective view of the distal end of the crimping device of FIG. 30, in a crimping configuration.
Figure 41:
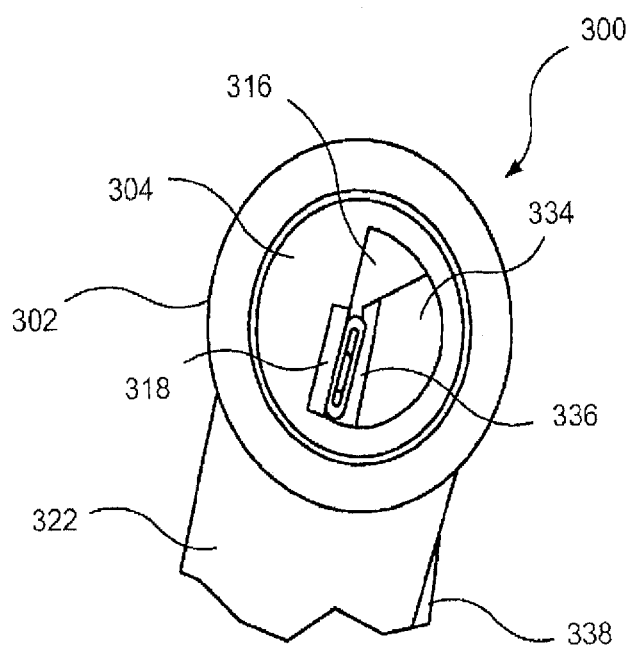
FIG. 41 shows a plan view of the distal end of the crimping device in the crimping configuration of FIG. 40.

After a desired tension has been applied to the cable 104, the handles 322, 338 are drawn toward one another to move the crimping device 300 to the crimping configuration, as shown in FIGS. 40-41. Drawing the handles 322, 338 toward one another rotates the first sleeve 302 and the second sleeve 304 relative to one another to move the first and second crimping edges 318, 336 toward one another. The first crimping edge 318 moves over the distal opening 332 crimping the deformable member 150 between the first and second crimping edges 318, 336 over the cable 104, fixing the cable 104 around the bone 108.

Figures 42, 43:
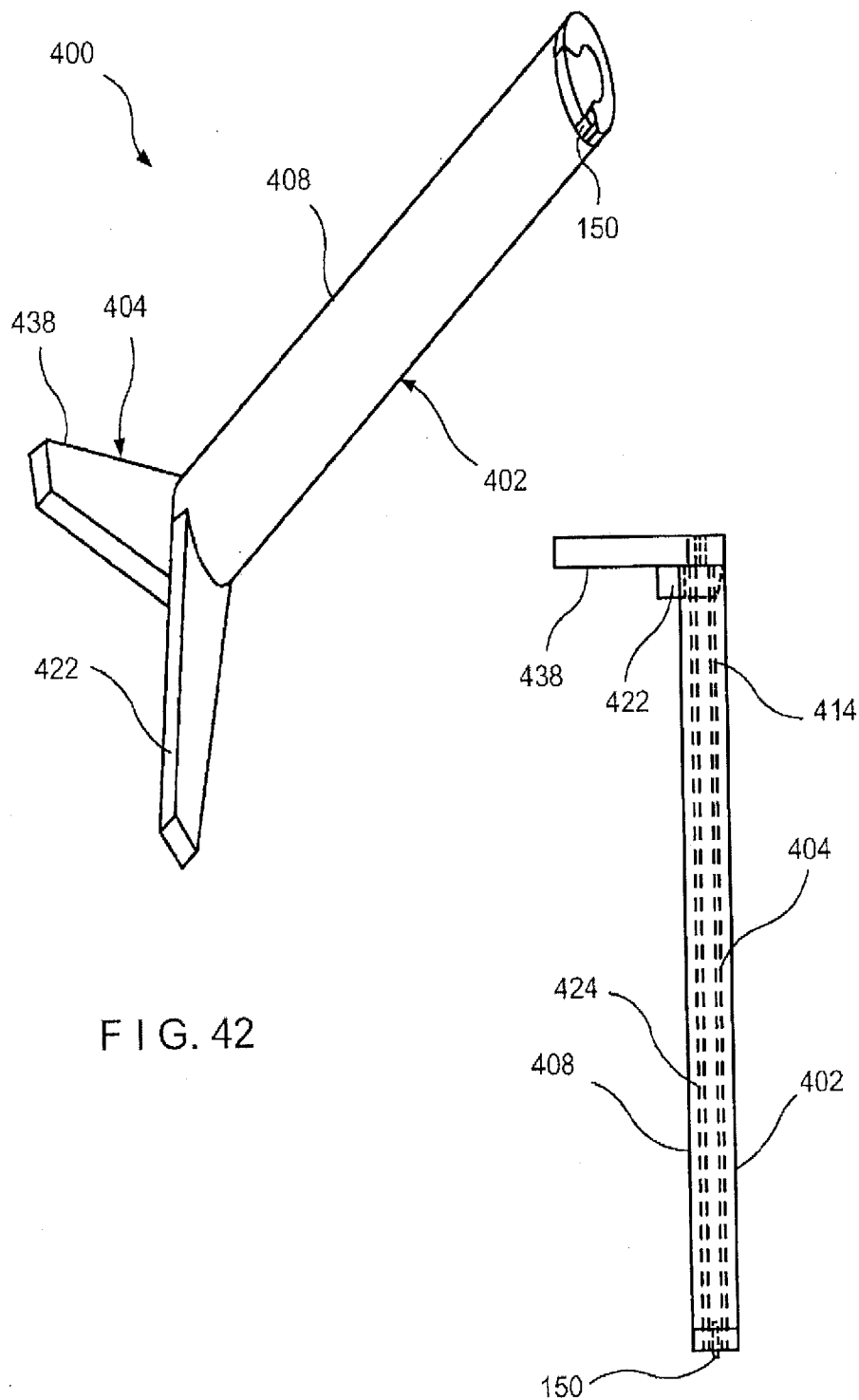
FIG. 42 shows a perspective view of a crimping device according to a third exemplary embodiment of the present invention.
FIG. 43 shows a side view of the crimping device of FIG. 42.

As shown in FIGS. 42-51, a crimping device 400 according to a third exemplary embodiment is substantially similar to the crimping device 300 described above excepted as noted below. As shown in FIGS. 42-43, the crimping device 400 comprises a first sleeve 402 and a second sleeve 404 nested within the first sleeve 402 such that the first and second sleeves 402, 404 are rotatable relative to one another about a longitudinal axis of the crimping device 400, between an open configuration and a crimping configuration. Similarly to the first sleeve 302, the first sleeve 402, as shown in FIGS. 44-46, includes a first longitudinal body 408 extending from a proximal end 410 to a distal end 412 and a handle 422 extending laterally from the proximal end 410. The first longitudinal body 408 also includes a first lumen 414 extending therethrough for accommodating a second longitudinal body 424 of the second sleeve 404. The first lumen 414, however, does not accommodate any portion of the deformable member 150 or the cable 104.

The first longitudinal body 408 further includes a groove 416 at the distal end 412. The groove 416 extends radially about a portion of the first lumen 414. To accommodate the deformable member 150 and the cable 104, the first sleeve 402 further includes a second lumen 442 extending longitudinally through the first longitudinal body 408, substantially parallel to the first lumen 414 such that the second lumen 442 extends through the groove 416. The second lumen 442 may extend through the longitudinal body 424 with a distal end 444 of the second lumen 444 adjacent to a first lateral surface 418 of the groove 416.

As shown in FIGS. 47-49, the second sleeve 404 may be substantially similar to the second sleeve 304. The second sleeve 404 includes the second longitudinal body 424 extending from a proximal end 426 to a distal end 428 and a handle 438 extending laterally from the proximal end 424. The longitudinal body 424, however, does not include a lumen extending therethrough. Rather, the second sleeve 404 includes an opening 430 through the handle 438, which aligns with the second lumen 442 when the crimp device 400 is in the open configuration to receive the cable 104 therethrough. The second longitudinal body 424 further includes a protrusion 434 that extends radially outward from the distal end 428. The protrusion 434 is sized and shaped so that when the crimp device 400 is in the open configuration the protrusion 434 is received within the groove 416 of the first sleeve 402, while exposing the second lumen 442. Thus, a second lateral surface 436 of the protrusion 434 does not cover any portion of the distal opening 444 of the second lumen 442.

In the open configuration, as shown in FIG. 50, the second lumen 442 is exposed between the first and second lateral surfaces 418, 436 such that the deformable member 150 may be received within the distal opening 444. The cable 104 extends through the channel 152 of the deformable member 150 and passes proximally through the second lumen 442 of the first sleeve 402 to extend proximally past the opening 430 in the handle 438 of the second sleeve 404. In the crimping configuration, as shown in FIG. 51, the first sleeve 402 and the second sleeve 404 are rotated relative to one another about the longitudinal axis such that the second lateral surface 436 is moved toward the first lateral surface 418 so that the deformable member 150 is crushed therebetween, thereby crimping the deformable member 150 over the cable 104. The first sleeve 402 and the second sleeve 404 may be rotated relative to one another by, for example, drawing the handles 422, 438 toward one another.

It will be apparent to those skilled in the art that various modifications and variations may be made in the structure and methodology of the present invention, without departing from the spirit or scope of the invention. Thus, it is intended that the present invention cover the modifications and variations of this invention provided that they come within the scope of the appended claims and their equivalents.

What is claimed is:

1. A method for treating a bone, comprising:
   circling a cable around a target bone to be treated, the cable extending from an enlarged first end to a distal second end;
   inserting the enlarged first end of the cable through a first lumen of a cable block and passing the distal second end through a second lumen of the cable block, the first lumen extending from a first lumen proximal opening in a proximal face of the cable block to a first lumen distal opening in a distal face of the cable block, the first lumen sized and shaped to pass the enlarged first end therethrough from the first lumen proximal opening to the first lumen distal opening, the second lumen extending from a second lumen proximal opening in the proximal face of the cable block to a second lumen distal opening in the distal face of the cable block, the cable block further including a slot connecting distal portions of the first and second lumens, the slot having a width sized to slidably receive the cable therethrough;
   displacing the enlarged first end of the cable laterally through the slot so that the enlarged end of the cable abuts a portion of the slot through which it cannot pass proximally;
   passing the second end of the cable through a lumen of a locking member and sliding the locking member over the cable until an end of the locking member abuts the cable block;
   applying a desired tension to the cable; and
   crimping the locking member over the cable to fix the cable around the target bone at the desired tension.

2. The method of claim 1, further comprising positioning a plate along a target portion of the target bone with the cable circled about both the bone and the plate, wherein the locking member fixes the cable at the desired tension to hold the plate against the target portion of the target bone.

3. The method of claim 2, wherein the plate includes a plurality of grooves along an edge of a surface thereof which faces away from the target bone, each of the grooves being sized and shaped to receive a width of the cable therein to prevent the cable from sliding longitudinally along the plate.

4. The method of claim 1, wherein crimping the locking member includes moving a crimping device from an open configuration in which the locking member and the cable may be slidably received therein to a crimping configuration in which first and second sleeves are rotated relative to one another about a longitudinal axis of the crimping device, the first sleeve including a third lumen extending therethrough, the second sleeve housed substantially within the third sleeve and including a fourth lumen extending therethrough.

5. The method of claim 4, wherein a diameter of a distal opening of the fourth lumen is smaller than a diameter of a portion the fourth lumen extending proximally therefrom and is off-center relative to the longitudinal axis, a diameter of a distal opening of the third lumen being smaller than a diameter of a portion of the third lumen extending proximally therefrom and is off-center relative to the longitudinal axis, the distal openings of the third and fourth lumens being aligned in the open configuration to receive the locking member therethrough and misaligned in the crimping configuration to crimp the locking member over the cable.

6. The method of claim 4, further comprising cutting a portion of the cable extending proximally from the locking member.

7. The method of claim 6, wherein cutting the cable includes moving the crimping device from the crimping configuration to a cutting configuration in which a third sleeve substantially housed within the fourth lumen of the second sleeve and including a fifth lumen extending therethrough is rotated relative thereto such that the fifth lumen is moved out of alignment with the distal openings of the third and fourth lumens to cut the portion of the cable proximal the locking member.

8. The method of claim 4, wherein the first sleeve includes a quadrant wheel extending laterally of the proximal end of the first longitudinal body and wherein the second sleeve includes a ratchet pawl engaging teeth of the quadrant wheel such that the first and second sleeves are selectively rotatably locked with respect to one another.

9. The method of claim 4, wherein the second longitudinal body includes a protrusion extending distally from a distal end thereof, an edge of the protrusion being adjacent to a distal opening of the fourth lumen, a distal opening of the third lumen being sized and shaped to receive the protrusion and expose the fourth lumen in the open configuration, the locking member being crimped between an edge of the distal opening and the edge of the protrusion as the first and second longitudinal members are moved to the crimping configuration.

10. The method of claim 4, wherein the first sleeve includes a sixth lumen and a recess at a distal end thereof extending radially about a portion of the third lumen, the sixth lumen extending parallel to the third lumen such that the sixth lumen extends through the recess adjacent to a lateral surface thereof, the sixth lumen being sized and shaped to receive the locking member and the cable therein, the second longitudinal body including a protrusion extending radially outward from a distal end thereof positioned so that the protrusion is received within the recess exposing the sixth lumen when in the open configuration, movement of the first and second longitudinal members to the crimping position crimping the locking member between a lateral surface of the protrusion and the lateral surface of the recess.

11. The method of claim 4, wherein moving the crimping device from the open configuration to the crimping configuration includes drawing a first handle extending laterally from a proximal end of the first sleeve and a second handle extending laterally from a proximal end of the second sleeve toward one another to rotate the first and second sleeves.

* * * * *